United States Patent
Wang et al.

(10) Patent No.: US 9,681,972 B2
(45) Date of Patent: *Jun. 20, 2017

(54) UNIFORM CRIMPING AND DEPLOYMENT METHODS FOR POLYMER SCAFFOLD

(71) Applicant: Abbott Cardiovascular Systems Inc., Santa Clara, CA (US)

(72) Inventors: Yunbing Wang, Sunnyvale, CA (US); Rommel Lumauig, San Jose, CA (US); James Oberhauser, Saratoga, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/918,318

(22) Filed: Oct. 20, 2015

(65) Prior Publication Data

US 2016/0038320 A1    Feb. 11, 2016

Related U.S. Application Data

(62) Division of application No. 13/438,211, filed on Apr. 3, 2012, now Pat. No. 9,199,408.

(51) Int. Cl.
*A61F 2/958* (2013.01)
*B23P 11/02* (2006.01)
(Continued)

(52) U.S. Cl.
CPC ............ *A61F 2/958* (2013.01); *B23P 11/005* (2013.01); *B23P 11/025* (2013.01); *B29C 53/02* (2013.01);
(Continued)

(58) Field of Classification Search
CPC .. A61F 2/962; A61F 2/958; A61F 2/91; A61F 2002/9522; B23P 11/025;
(Continued)

(56) References Cited

U.S. PATENT DOCUMENTS 5,836,965 A   11/1998   Jendersee et al.
5,913,871 A   6/1999    Werneth et al.
(Continued)

FOREIGN PATENT DOCUMENTS

EP   0 787 020   5/1996
EP   1 226 798   5/2000
(Continued)

OTHER PUBLICATIONS

Bosiers et al., "Coronary and endovascular applications of the Absorb™ bioresorbable vascular scaffold", Interv. Cardiol. 4(6), pp. 621-631 (2012).

(Continued)

*Primary Examiner* — Jermie Cozart
(74) *Attorney, Agent, or Firm* — Squire Patton Boggs (US) LLP

(57) ABSTRACT

A medical device-includes a scaffold crimped to a catheter having an expansion balloon. The scaffold is crimped to the balloon by a process that includes one or more balloon pressurization steps. The balloon pressurization steps are selected to enhance scaffold retention to the balloon and maintain a relatively uniform arrangement of balloon folds about the inner surface of the crimped scaffold so that the scaffold expands in a uniform manner when the balloon is inflated.

23 Claims, 15 Drawing Sheets

(51) Int. Cl.
  *B29C 53/02* (2006.01)
  *B23P 11/00* (2006.01)
  *B29L 31/00* (2006.01)
  *B29K 67/00* (2006.01)
  *A61F 2/915* (2013.01)
  *A61F 2/95* (2013.01)

(52) U.S. Cl.
  CPC ....... *A61F 2/915* (2013.01); *A61F 2002/9522* (2013.01); *B29C 2793/0009* (2013.01); *B29K 2067/046* (2013.01); *B29K 2995/006* (2013.01); *B29L 2031/7534* (2013.01); *Y10T 29/49865* (2015.01); *Y10T 29/49913* (2015.01)

(58) Field of Classification Search
  CPC ......... Y10T 29/49913; Y10T 29/49929; Y10T 29/49865
  See application file for complete search history.

(56) References Cited

U.S. PATENT DOCUMENTS

| | | | |
|---|---|---|---|
| 5,976,181 A | 11/1999 | Whelan et al. | |
| 6,063,092 A | 5/2000 | Shin | |
| 6,629,350 B2 | 10/2003 | Motsenbocker | |
| 6,666,880 B1 | 12/2003 | Chiu et al. | |
| 6,745,445 B2 | 6/2004 | Spilka | |
| 6,863,683 B2 | 3/2005 | Schwager et al. | |
| 7,010,850 B2 | 3/2006 | Hijlkema et al. | |
| 7,316,148 B2 | 1/2008 | Asmus et al. | |
| 7,761,968 B2 | 7/2010 | Huang et al. | |
| 7,951,185 B1 | 5/2011 | Abbate et al. | |
| 8,002,817 B2 | 8/2011 | Limon et al. | |
| 8,046,897 B2 | 11/2011 | Wang et al. | |
| 8,123,793 B2 | 2/2012 | Roach et al. | |
| 8,261,423 B2 | 9/2012 | Jow et al. | |
| 8,726,483 B2 | 5/2014 | Stankus et al. | |
| 8,961,848 B2 | 2/2015 | Roberts et al. | |
| 9,199,408 B2 * | 12/2015 | Wang ..................... B29C 53/02 | |
| 2002/0143382 A1 | 10/2002 | Hijlkema et al. | |
| 2004/0078953 A1 | 4/2004 | Spilka | |
| 2004/0106973 A1 | 6/2004 | Johnson | |
| 2004/0138731 A1 | 7/2004 | Johnson | |
| 2005/0119720 A1 | 6/2005 | Gale et al. | |
| 2005/0143752 A1 | 6/2005 | Schwager et al. | |
| 2006/0047336 A1 | 3/2006 | Gale et al. | |
| 2006/0100694 A1 | 5/2006 | Globerman | |
| 2007/0006441 A1 | 1/2007 | McNiven et al. | |
| 2007/0204455 A1 | 9/2007 | Knott et al. | |
| 2007/0271763 A1 | 11/2007 | Huang et al. | |
| 2007/0282433 A1 | 12/2007 | Limon et al. | |
| 2007/0289117 A1 | 12/2007 | Huang et al. | |
| 2008/0016668 A1 | 1/2008 | Huang et al. | |
| 2008/0033523 A1 | 2/2008 | Gale et al. | |
| 2008/0033524 A1 | 2/2008 | Gale | |
| 2008/0147164 A1 | 6/2008 | Gale et al. | |
| 2008/0275537 A1 | 11/2008 | Limon | |
| 2009/0001633 A1 | 1/2009 | Limon et al. | |
| 2009/0088829 A1 | 4/2009 | Wang et al. | |
| 2009/0105800 A1 | 4/2009 | Sabaria | |
| 2010/0004735 A1 | 1/2010 | Yang et al. | |
| 2010/0025894 A1 | 2/2010 | Kleiner et al. | |
| 2010/0063571 A1 | 3/2010 | Roach et al. | |
| 2010/0323091 A1 | 12/2010 | Castro et al. | |
| 2011/0190872 A1 | 8/2011 | Anukhin et al. | |
| 2011/0270383 A1 | 11/2011 | Jow et al. | |
| 2011/0271513 A1 | 11/2011 | Wang | |
| 2012/0010693 A1 | 1/2012 | Van Sciver | |
| 2012/0042501 A1 | 2/2012 | Wang et al. | |
| 2012/0079706 A1 | 4/2012 | Knott et al. | |

FOREIGN PATENT DOCUMENTS

| | | |
|---|---|---|
| EP | 1 295 570 | 7/2002 |
| EP | 2 029 052 | 3/2003 |
| WO | WO 99/55406 | 11/1999 |
| WO | WO 02/102283 | 12/2002 |
| WO | WO 2005/053937 | 6/2005 |
| WO | WO 2006110861 | 10/2006 |
| WO | WO 2007/146354 | 12/2007 |
| WO | WO 2008/033621 | 3/2008 |
| WO | WO 2010/151497 | 12/2010 |

OTHER PUBLICATIONS

Miller "Abbott's Bioresorbable Stent Shows Durable Results in ABSORB Trial", The Gray Sheet, pp. 17-18, Mar. 2003.

* cited by examiner

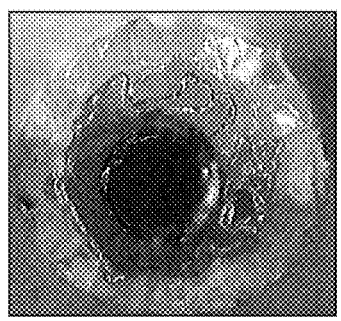 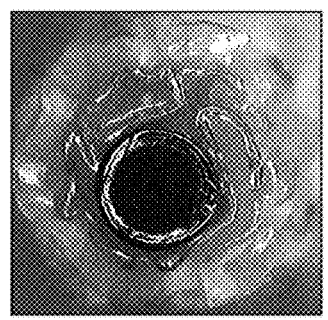 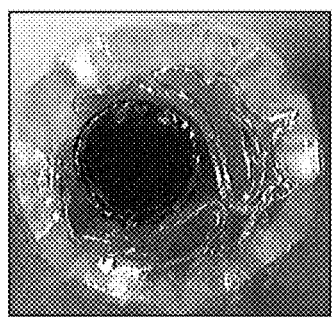
FIG. 9A    FIG. 9B    FIG. 9C
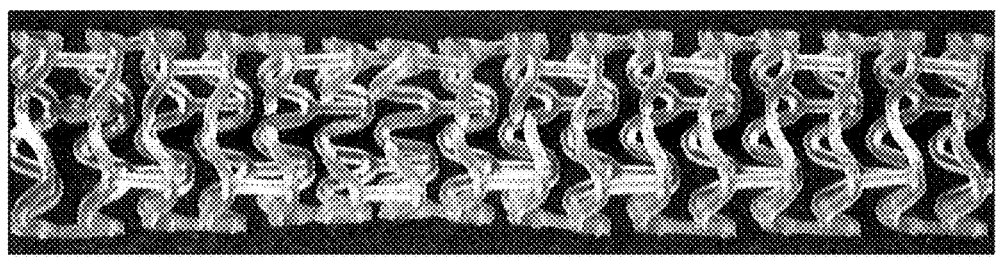
FIG. 10

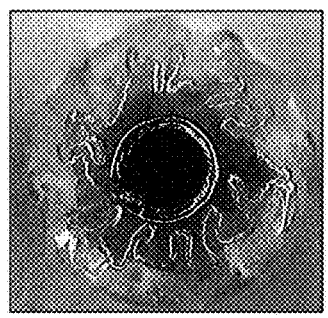 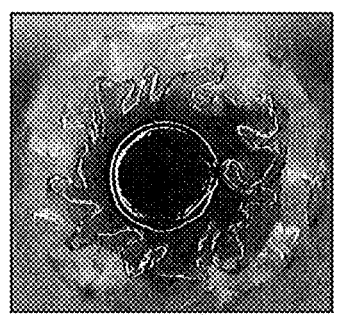 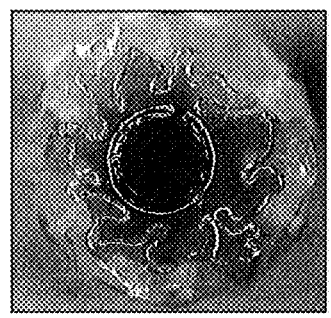
FIG. 11A  FIG. 11B  FIG. 11C
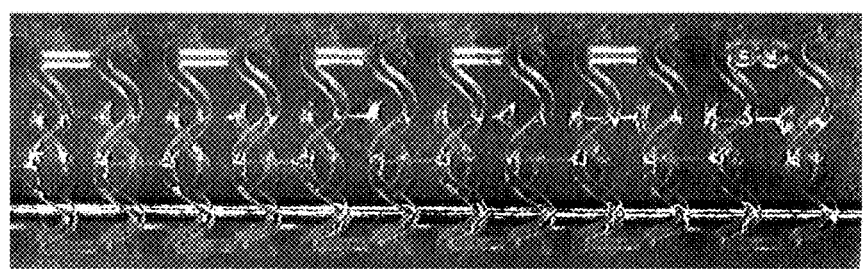
FIG. 12

UNIFORM CRIMPING AND DEPLOYMENT METHODS FOR POLYMER SCAFFOLD

BACKGROUND OF THE INVENTION

Field of the Invention

The present invention relates to drug-eluting medical devices; more particularly, this invention relates to processes for crimping a polymeric scaffold to a delivery balloon.

Background of the Invention

The art recognizes a variety of factors that affect a polymeric scaffold's ability to retain its structural integrity when subjected to external loadings, such as crimping and balloon expansion forces. According to the art, characteristics differentiating a polymeric, bio-absorbable scaffolding of the type expanded to a deployed state by plastic deformation from a similarly functioning metal stent are many and significant. Indeed, several of the accepted analytic or empirical methods/models used to predict the behavior of metallic stents tend to be unreliable, if not inappropriate, as methods/models for reliably and consistently predicting the highly non-linear behavior of a polymeric load-bearing portion of a balloon-expandable scaffold (hereinafter "scaffold"). The models are not generally capable of providing an acceptable degree of certainty required for purposes of implanting the scaffold within a body, or predicting/anticipating the empirical data.

Polymer material considered for use as a polymeric scaffold, e.g. poly(L-lactide) ("PLLA"), poly(L-lactide-co-glycolide) ("PLGA"), poly(D-lactide-co-glycolide) or poly(L-lactide-co-D-lactide) ("PLLA-co-PDLA") with less than 10% D-lactide, and PLLD/PDLA stereo complex, may be described, through comparison with a metallic material used to form a stent, in some of the following ways. A suitable polymer has a low strength to weight ratio, which means more material is needed to provide an equivalent mechanical property to that of a metal. Therefore, struts must be made thicker and wider to have the required strength for a stent to support lumen walls at a desired radius. The scaffold made from such polymers also tends to be brittle or have limited fracture toughness. The anisotropic and rate-dependant inelastic properties (i.e., strength/stiffness of the material varies depending upon the rate at which the material is deformed) inherent in the material, only compound this complexity in working with a polymer, particularly, bio-absorbable polymer such as PLLA or PLGA.

One challenge to a peripheral scaffold is crimping to a balloon and expansion of the scaffold when the balloon is inflated. Problems arise where, on the one hand, the scaffold cannot be crimped to the desired size without introducing structural failure, i.e., fracture, or excessive cracking, either in the crimped state or when expanded from the crimped state by a balloon. On the other hand, a scaffold can be crimped and deployed, yet deploys with non-uniformity in its deployed state. In these cases the scaffold is susceptible to acute or fatigue failure as the irregularly-deployed rings and/or cells, loaded beyond their design limits as a consequence of the non-uniform deployment, have a reduced acute or fatigue life within the vessel.

Additionally, the retention force keeping a crimped scaffold on a delivery balloon during transit through tortuous anatomy is sometimes not sufficiently high to preclude pre-mature dislodgment of the scaffold from the balloon. If the scaffold is not held on the balloon with sufficient force, e.g., as where there is recoil in the scaffold following crimping or the coefficient of friction between balloon and scaffold is too low, the scaffold can become separated from the balloon as the catheter distal end flexes and/or impinges on walls of the delivery sheath. For a metallic stent, there are several well-known approaches for increasing the retention of the stent to a balloon during transit to the target site. However, methods proposed thus far for retaining the scaffold on a balloon are in need of improvement, or inappropriate for a polymer scaffold.

In one example of a method for crimping a metallic stent to a delivery balloon, the stent is placed in a crimper and the temperature elevated to facilitate greater compliance in the balloon material to allow material to extend between gaps in the stent struts. Additionally, balloon pressure is maintained while the stent is being crimped to increase stent retention to the balloon. After an initial pre-crimp, the stent is placed on the delivery balloon and allowed to slightly recoil under balloon pressure and while the stent has an elevated temperature. After this step, the stent is crimped onto the balloon while the balloon is pressurized. The stent is cycled through larger and smaller diameters. Additionally, balloon pressure may be supplied in bursts or held constant during these crimping steps. Further details of this process may be found in U.S. application Ser. No. 12/895,646 filed Sep. 30, 2010.

The art previously devised methods for retaining a balloon-expanded polymer scaffold on a delivery balloon. In one example, the scaffold is crimped to the delivery balloon at a temperature well below the polymer's TG. Then the scaffold, disposed between ends of the balloon, is thermally insulated from the balloon's ends. The ends of the balloon are then heated to about 185 degrees Fahrenheit to expand the diameter of the balloon material at its ends. The expanded balloon ends form raised edges abutting the scaffold ends to resist dislodgment of the scaffold from the balloon. In one example, this process provided a retention force of about 0.35 lb. for a Poly (L-lactide) (PLLA) scaffold crimped to a polymide-polyether block co-polymer (PE-BAX) balloon. An example of this process is disclosed in U.S. Pat. No. 6,666,880.

Another example of a polymer scaffold crimping is found in U.S. Pat. No. 8,046,897, which has a common inventor with the present application. According to the '897 patent the balloon is inflated, or partially inflated before crimping. The scaffold is placed on the balloon. The crimping may take place at elevated temperatures, e.g., 30-50 degrees Celsius.

A film-headed crimper has been used to crimp stents to balloons. Referring to FIG. 8A, there is shown a perspective view of a crimping assembly 20 that includes three rolls 123, 124, 125 used to position a clean sheet of non-stick material between the crimping blades and the stent prior to crimping. For example, upper roll 125 holds the sheet secured to a backing sheet. The sheet is drawn from the backing sheet by a rotating mechanism (not shown) within the crimper head 20. A second sheet is dispensed from the mid roll 124. After crimping, the first and second (used) sheets are collected by the lower roll 123. As an alternative to rollers dispensing a non-stick sheet, a stent may be covered in a thin, compliant protective sheath before crimping.

FIG. 8B illustrates the positioning the first sheet 125a and second sheet 124a relative to the wedges 22 and a stent 100 within the aperture of the crimping assembly 20. As illustrated each of the two sheets are passed between two blades 22 on opposite sides of the stent 100 and a tension T1 and T2 applied to gather up excess sheet material as the iris of the crimping assembly is reduced in size via the converging blades 22.

The dispensed sheets of non-stick material (or protective sheath) are used to avoid buildup of coating material on the crimper blades for stents coated with a therapeutic agent.

The sheets 125a, 124a are replaced by a new sheet after each crimping sequence. By advancing a clean sheet after each crimp, accumulation of contaminating coating material from previously crimped stents is avoided. By using replaceable sheets, stents having different drug coatings can be crimped using the same crimping assembly without risk of contamination or buildup of coating material from prior stent crimping.

There is a continuing need to improve upon methods for crimping a polymer scaffold to a delivery balloon in order to improve upon the uniformity of deployment of a polymer scaffold from the balloon, to increase the retention force between scaffold and balloon, and to obtain a minimal crossing profile for delivery of the scaffold to a target site.

SUMMARY OF THE INVENTION

The invention provides methods for increasing uniformity of polymer scaffold expansion via a balloon inflated delivery system, while maintaining or improving upon scaffold-balloon retention. A preferred use for the invention is crimping a coronary scaffold to a delivery balloon.

It has been demonstrated that the retention force of a crimped polymer scaffold on a delivery balloon may be increased by a crimping process that includes crimping the scaffold to the balloon while the balloon is pressurized; that is, the balloon is pressurized at the same time as the scaffold's outer diameter is being reduced by crimper blades. Additional features of such a crimping process include heating the scaffold to a temperature close to the glass transition temperature (TG) of the polymer material and applying balloon pressure during dwell periods (i.e., balloon pressure is applied when the scaffold diameter is held constant).

For a balloon-expanded polymer scaffold it was found that processes for crimping the scaffold to the balloon, in order to ensure safe delivery to an implant site, expansion and implantation of an intact scaffold were in need of modification. In particular, it was found that certain modifications were needed to ensure that all three of the following requirements for a crimping process would be met:

Structural integrity: avoiding damage to the scaffold's structural integrity when the scaffold is crimped to the balloon, or expanded by the balloon.

Safe delivery to an implant site: avoiding dislodgement or separation of the scaffold from the balloon during transit to an implant site.

Uniformity of expansion: avoiding non-uniform expansion of scaffold rings, which can lead to structural failure and/or reduced fatigue life.

Regarding the uniformity of expansion requirement, it has been recently found that earlier crimping processes, while satisfying the other two requirements, have not consistently expanded in a uniform manner when the balloon is expanded. As a consequence, ring struts and/or cell structures, which provide radial strength and stiffness for the scaffold, inherit an un-even distribution of stresses and strains. Over-expanded cells are called upon to sustain higher-than-normal stresses and strains while neighboring under-expanded cells are underutilized. The balloon-induced stresses and strains associated with over-expanded cells can exceed the material's ultimate stress and strain level at deployment, which might potentially result in crack formation or fracture, or exhibit a reduced fatigue life or fracture toughness, in which case fracture can occur immediately, after a few days, or after weeks of implantation.

In view of the foregoing objectives, the invention provides crimping processes for improving upon the uniformity of expansion of a polymer scaffold crimped to a balloon including the step of inflating the delivery balloon for substantially the entire crimp. For example, the delivery balloon may be inflated when the scaffold is placed on the balloon and just prior to inserting the balloon and scaffold within a crimper head, then maintaining about this pressurization until after the scaffold diameter has been decreased to about 50% or more of its pre-crimp diameter.

In one embodiment, the balloon is pressurized until just prior to a final crimping step. For example, the balloon is pressurized until a final crimping step that reduces the scaffold diameter by an additional about 25%, or by an additional about 10%.

Balloon pressurization may be set at a constant value, e.g., between 20-70 psi, or the balloon pressure may be set at a plurality of values during crimping. For example, balloon pressure may be decreased after the scaffold has reached a certain crimping diameter, e.g., after the scaffold diameter has decreased by about 40-50%. In one example, there are two programmed balloon pressure settings (high and low) corresponding to, respectively, a high and low diameter for the scaffold during the crimping process, e.g., about 150 psi and between about 20-70 psi.

In another embodiment, a crimping process includes balloon pressurization while the scaffold to balloon diameter is sufficiently large to allow substantially all of the pre-arranged folds of the balloon to be removed. In this inflated state, the scaffold is then crimped to the balloon until the scaffold diameter has been reduced in size to about 50% (or more).

According to another embodiment, a crimping process including balloon pressurization prior to and during crimping produces a crimped scaffold and balloon whereby substantially all pre-arranged folds are removed when the scaffold-balloon are in a fully-crimped state (e.g., at the point in time when a restraining sheath is placed over the scaffold and balloon to limit recoil).

According to another embodiment, the crimping steps may include only 1, or only 3, or at most 3 dwell three dwell periods between an initial diameter reduction and final diameter reduction.

According to another embodiment, a crimping process reduces a scaffold diameter to only 30% to its pre-crimp size. According to this process the scaffold diameter is reduced by an additional about 60-70% after an initial crimp and there is no dwell period when the scaffold is reduced in diameter by the additional about 60-70%.

In a preferred embodiment the crimping process includes an alignment check. The balloon inflated state is preferably maintained during the alignment check. In other embodiments one may dispense with the alignment check, so that the scaffold is removed from the crimper only after it is fully crimped to the balloon.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

BRIEF DESCRIPTION OF THE DRAWINGS

FIGS. 9A-9C are photographs of the cross-section of a scaffold having a pre-crimp pattern as shown in FIG. 7 when crimped to a balloon of a balloon catheter. FIG. 9A shows the cross-section shape of balloon folds near the distal end of the balloon. FIG. 9B shows the cross-section shape of balloon folds near the middle of the balloon. FIG. 9C shows the cross-section shape of balloon folds near the proximal end of the balloon. The crimped scaffold and balloon of FIGS. 9A-9C was obtained using the process of FIGS. 1A-1B.

FIG. 10 is a photograph showing a scaffold having a pattern similar to that shown in FIG. 7 after balloon expansion. The scaffold shown in this picture was expanded using the process of FIGS. 1A-1B. As shown in this photograph, the scaffold exhibits a non-uniform expansion and there are fractures in the rings of the scaffold.

FIGS. 11A-11C are photographs of the cross-section of a scaffold having a pre-crimp pattern as shown in FIG. 7 when crimped to a balloon of a balloon catheter. FIG. 11A shows the cross-section shape of balloon folds near the distal end of the balloon. FIG. 11B shows the cross-section shape of balloon folds near the middle of the balloon. FIG. 11C shows the cross-section shape of balloon folds near the proximal end of the balloon. The crimped scaffold and balloon of FIGS. 11A-11C was obtained using the process of FIGS. 4A-4B.

FIG. 12 is a photograph showing a scaffold having a pattern similar to that shown in FIG. 7 after balloon expansion. The scaffold shown in this picture was expanded using the process of FIGS. 4A-4B. As shown in this photograph, the scaffold exhibits a more uniform expansion and there are no fractures in the rings of the scaffold.

DETAILED DESCRIPTION OF EMBODIMENTS

Figure 1A:
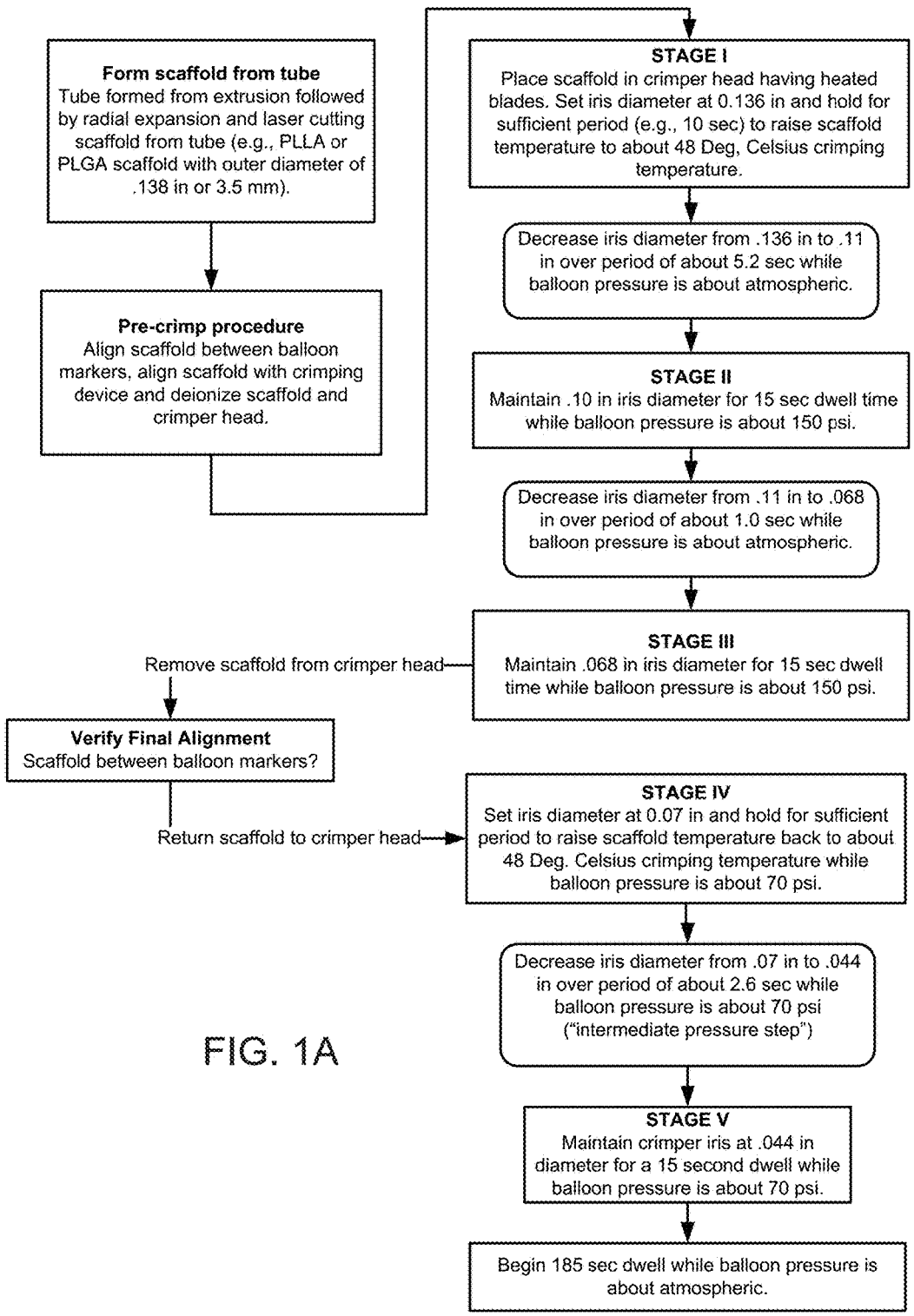
FIG. 1A is an example of a flow process for crimping a polymer scaffold to a balloon.

The "glass transition temperature," TG, is the temperature at which the amorphous domains of a polymer generally change from a brittle, vitreous state to a solid deformable or ductile state at atmospheric pressure. In other words, the TG corresponds to the temperature where the onset of noticeable segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. TG of a given polymer can be dependent on the heating rate and can be influenced by the thermal history of the polymer. Furthermore, the chemical structure of the polymer heavily influences the glass transition by affecting mobility.

Poly(lactide-co-glycolide) (PLGA) and Poly (L-lactide) (PLLA) are examples of a class of semi-crystalline polymers that may be used to form the scaffolds described herein. PLLA is a homopolymer and PLGA is a co-polymer. The percentage of glycolide (GA) in a scaffold constructed of PLGA may vary, which can influence the lower range of TG. For example, the percentage of GA in the matrix material may vary between 0-15%. For PLLA, the onset of glass transition occurs at about 55 degrees Celsius. With an increase of GA from about 0% to 15% the lower range for TG for PLGA can be correspondingly lower by about 5 degrees Celsius. For PLGA having % GA of about 5% the temperature ranges for crimping may be between about 46 to 53 degrees Celsius. For PLGA having % GA of about 15% the temperature ranges for crimping are about 43 to 50 degrees Celsius.

In one embodiment, a tube is formed by an extrusion of PLLA. The tube forming process described in US Pub. No. 2010/00025894 may be used to form this tube. The finished, solidified polymeric tube of PLLA may then be deformed in radial and axial directions by a blow molding process wherein deformation occurs progressively at a predetermined longitudinal speed along the longitudinal axis of the tube. For example, blow molding can be performed as described in U.S. Publication No. 2009/0001633. This biaxial deformation, after the tube is formed, can produce noticeable improvement in the mechanical properties of the scaffold structural members cut from the tube without this expansion. The degree of radial expansion that the polymer tube undergoes characterizes the degree of induced circumferential molecular or crystal orientation. In a preferred embodiment, the radial expansion ratio or RE ratio is about 450% of the starting tube's inner diameter and the axial expansion ratio or AE ratio is about 150% of the starting tube's length. The ratios RA and AE are defined in U.S. Pub. No. 2010/00025894.

A scaffold's outer diameter (made according to the foregoing processes) may be designated by where it is expected to be used, e.g., a specific location or area in the body. The outer diameter, however, is usually only an approximation of what will be needed during the procedure. For instance, there may be extensive calcification that breaks down once a therapeutic agent takes effect, which can cause the scaffold to dislodge in the vessel. Further, since a vessel wall cannot be assumed as circular in cross-section, and its actual size only an approximation, a physician can choose to overextend the scaffold to ensure it stays in place. For this reason, it is sometimes preferred to use a tube with a diameter larger than the expected deployed diameter of the scaffold.

As discussed earlier, fabrication of a scaffold presents challenges that are not present in metallic stents. One challenge, in particular, is the fabrication of a scaffold, which means the load bearing network of struts including connectors linking ring elements or members that provide the radial strength and stiffness needed to support a lumen. In particular, there exists an ongoing challenge in fabricating a scaffold that is capable of undergoing a significant degree of plastic deformation without loss of strength, e.g., cracks or fracture of struts. In one embodiment the ratio of deployed to fully crimped diameter is about 2.5. In this embodiment, the crimped diameter corresponds to an outer diameter that is only about 40% of the starting diameter. Hence, when deployed the drug eluting scaffold is expected to increase in size at least to about 2.5 times its crimped diameter size.

In one particular example, a scaffold is formed from a bi-axially expanded tube having an outer diameter of 3.5 mm, which approximately corresponds to a deployed diameter (the scaffold may be safely expanded up to 4.0 mm within a lumen). The iris of the crimping mechanism reaches a diameter of 0.044 in, which is maintained for a 185 sec dwell period (i.e., scaffold held at 0.044 in outer diameter within crimping mechanism). When later removed from the crimper, the scaffold will recoil despite there being a restraining sheath placed over the scaffold immediately after the scaffold is removed from the crimper. The scaffold and sheath are then subjected to radiation sterilization. At the point of use, i.e., at the point in time when a medical specialist removes the restraining sheath, the scaffold has an outer diameter of about 0.052 in (1.32 mm), or about 35-40% of the starting tube diameter of 3.5 mm. When in the crimping mechanism the scaffold reaches about 30-35% of the starting tube size.

An additional challenge faced with the scaffold is the ability of the scaffold to be crimped to the balloon so that an adequate retention force is established between the scaffold and balloon. A "retention force" for a scaffold crimped to a balloon means the maximum force applied to the scaffold along the direction of travel through a vessel that the scaffold-balloon is able to resist before dislodging the scaffold from the balloon. The retention force for a scaffold on a balloon is set by a crimping process, whereby the scaffold is plastically deformed onto the balloon surface to form a fit that resists dislodgment of the scaffold from the balloon. Factors affecting the retention of a scaffold on a balloon are many. They include the extent of surface-to-surface contact between the balloon and scaffold, the coefficient of friction of the balloon and scaffold surfaces, and the degree of protrusion or extension of balloon material between struts of the scaffold. As such, the magnitude of a pull off or retention force for a scaffold generally varies with its length. The shorter scaffold, therefore, is more likely to dislodge from the balloon as the catheter is pushed through tortuous anatomy than a longer scaffold where the same crimping process is used for both the longer and shorter scaffolds.

For a metal stent there are a wide variety of methods known for improving the retention force of a stent on a balloon via modification of one or more of the foregoing properties; however, many are not suitable or of limited usefulness for a scaffold, due to differences in mechanical characteristics of a scaffold verses a metal stent, as discussed earlier. Most notable among these differences is brittleness of polymer material suitable for balloon-expanded scaffold fabrication, verses that of a metal stent, and the sensitivity of the polymer material to heat. Whereas a metal stent may be deformed sufficiently to obtain a desired retention force, the range of deformation available to a polymer scaffold, while avoiding cracking or fracture-related problems, by comparison, is quite limited. The application of heat has been shown as effective for increasing retention forces for metal stents. However, the heat levels used can cause detrimental effects to the polymer material since they tend to correspond to temperatures well within, or above the TG of the material. For this reason, known heat methods for increasing retention forces for metal stents tend to be viewed as inappropriate for increasing a retention force between a scaffold and balloon.

It has been more of a challenge to achieve high retention forces for a crimped polymer scaffold, as compared to a crimped metal stent, for basically two reasons. First, there is less space available between struts in a crimped state, which prevents balloon material from extending between struts. As a result, there is less abutment or interference between struts and balloon material, which interference/abutment has previously been relied upon to increase the retention force of a metal stent on a balloon. This condition is a result of the need to fabricate wider and thicker struts for the scaffold, as compared to a metal stent, so as to provide adequate, deployed radial strength. Additionally, metal stents may be cut from a tube closer to the crimp diameter whereas a polymer scaffold may be cut from a tube at about the fully expanded diameter, which further reduces the space between struts in the crimped configuration. Second, a polymer is more sensitive to temperature ranges that have previously been used to increase retention to a balloon. Heating of a scaffold to within, or above TG induces significant changes in the molecular orientation of the polymer material that result in loss of strength when the scaffold is plastically deformed to its deployed diameter.

U.S. patent application Ser. No. 12/772,116 filed Apr. 30, 2010 (US20110270383) ('116 application) discusses a study that was conducted to investigate the effects on retention forces for crimped scaffolds. Principally, this study identified a temperature range relative to a TG of the scaffold material that improved retention forces without detrimentally affecting scaffold mechanical properties when deployed to support a vessel. For PLLA it was found that modifying the pressure and hold time of the scaffold for crimping temperatures of between about 40° and 55° C. improved the scaffold retention, with about 45-51° C. and about 48° C. being preferred temperatures for a PLLA scaffold. Additionally, the '116 application found that retention forces could be improved if the scaffold were crimped down to an intermediate diameter and then the balloon is deflated then re-inflated, followed by crimping the scaffold down to a final crimp diameter. The '116 application also contemplates similar results for PLGA, if TG for this material is taken into consideration and assuming other characteristics of the process and scaffold pattern. For PLGA having % GA of about 5% the temperature ranges for crimping may be between about 46 to 53 degrees Celsius. For PLGA having % GA of about 15% the temperature ranges for crimping are about 43 to 50 degrees Celsius.

When the scaffold is crimped to a balloon while being heated to temperatures well within the range of TG for the scaffold polymer, there is a greater tendency for polymer chain re-alignment to occur that will result in loss of strength when the scaffold is later deployed. Unacceptable crack formation (either in the number or extent of cracks), voids or outright fracture was observed in subsequent testing. If the crimping temperature is raised too high relative to the TG of the polymer, the memory of the matrix material at the starting tubing diameter is being removed, or reformed as the scaffold is deformed. As a consequence, when the scaffold is later expanded under physiological conditions, e.g., body temperature; it becomes more susceptible to crack formation due to its brittle properties at body temperatures and lack of chain alignment from its starting diameter. Retention force and scaffold integrity when crimped to the balloon generally improves at higher temperatures, however, the scaffold loses its structural integrity when later deployed if the temperature is raised too high, e.g., above TG. On the other hand, when the scaffold is heated to temperatures below about 15 degrees Celsius of the glass transition temperature, or not heated at all, there is no noticeable improvement in scaffold retention. It was found that the most effective range was between about 15 degrees below and up to about TG.

The '116 application explains that the above and related unexpected results may be explained in the following manner. When a polymer scaffold is crimped at a temperature slightly below its TG (e.g., from 5 to 15 degrees Celsius below TG), there are very short chains of the matrix material that are able to freely move to assist in the deformation of the scaffold without exceeding material stress limits. At the same time, the longer chains of the matrix substantially maintain their alignment, and, thus, stay intact without losing their orientation set when the starting tube was expanded. By doing so, the scaffold may be crimped down to a diameter for good scaffold retention, while the orientation of a majority of polymer chains would be the same to ensure desirable strength and fracture toughness in the final product, i.e., when the scaffold is deployed to support a vessel.

FIG. 1 of the '116 application shows a flow for a crimping process for a 3.0 mm (0.118 in) scaffold that is crimped to a final crimp diameter of 0.044 in. The diameter reduction from 0.118 in to 0.044 in includes three intermediate crimping diameters of 0.083 in, 0.063 in and 0.07 in, following a "pre-crimp" procedure in which the PLLA scaffold temperature is raised to a temperature of about 48° C. When the scaffold has attained the intermediate crimp diameters, the crimper jaws are held at the crimping diameter for a dwell period of 30 sec, 15 sec and 10 sec, respectively. After the final crimp diameter has been obtained, the crimp jaws are held at the final crimp diameter for about 200 sec. The delivery balloon, i.e., a PEBAX balloon, is inflated to a pressure of 17 psi for the dwell period 30, 15 and 10 second dwell periods. The dwell periods for the intermediate crimping stages are included in the process to allow for stress relaxation in the polymer material before decreasing the scaffold diameter further. Before the crimper iris is reduced by actuation of the crimper jaws, the balloon is deflated. Thus, in the example from the '116 application whenever the scaffold diameter is decreased, the balloon is not inflated.

Notwithstanding improved results in stent retention when practicing inventions described in the '116 application, it is desirable to further increase a scaffold retention force. For example, for a coronary scaffold it is desirable to have a balloon-scaffold retention force (i.e., force required to pull scaffold off balloon) of at least 0.7 lbs and preferably over 1.0 lbs.

Processes are proposed for achieving a high retention force while maintaining the structural integrity of a crimped polymer scaffold. One such process is described in co-pending application Ser. No. 13/089,225 (the '225 application) having a common assignee as this application. According to this disclosure, methods are proposed that increase the retention force on an 18 mm length, 3.5 mm pre-crimp diameter scaffold by at least 0.5 lbs over the process used to produce the data in the '116 application.

Figure 1B:
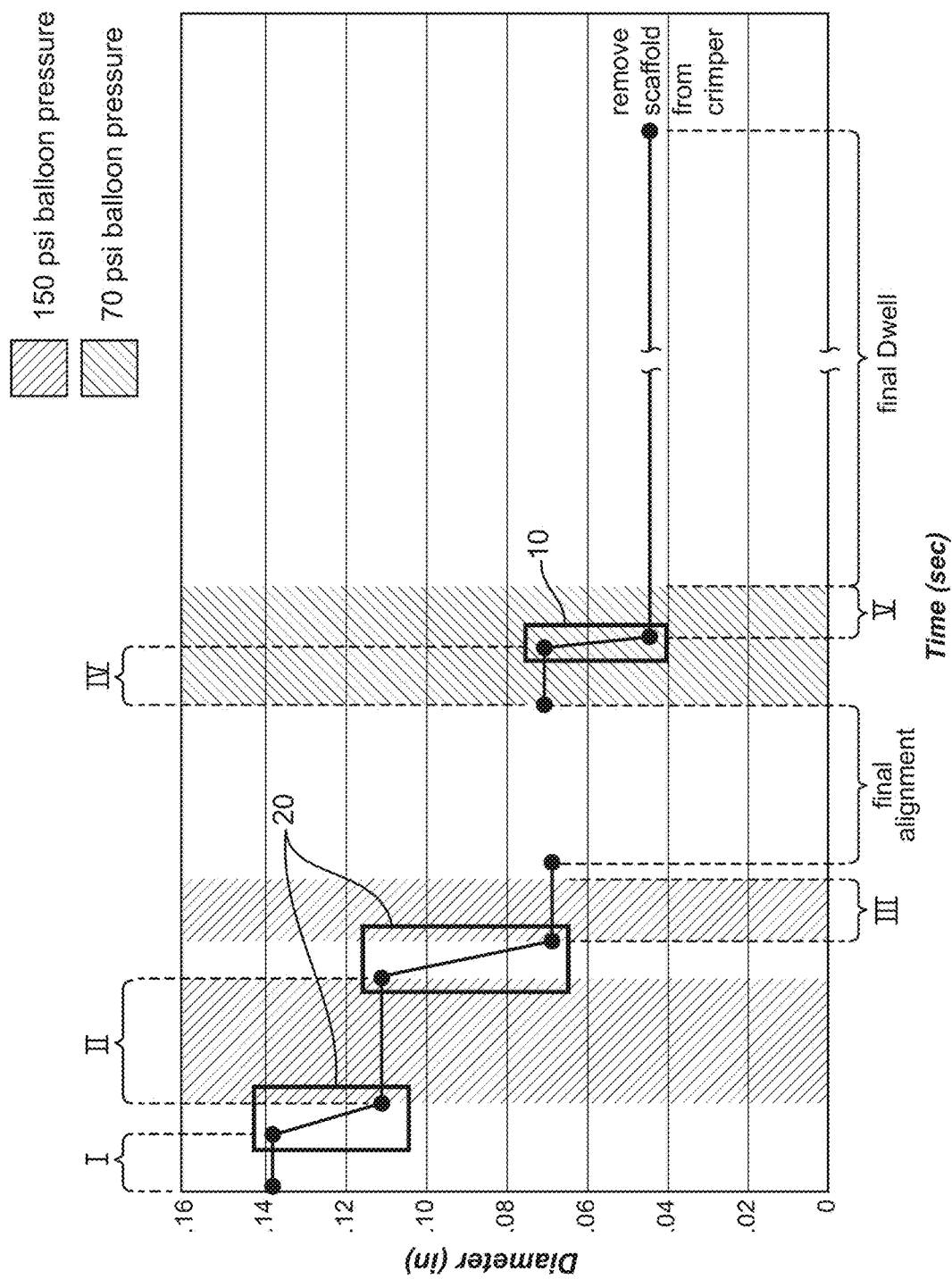
FIG. 1B shows the crimping portion of the FIG. 1A flow process in graphical form, plotting scaffold diameter vs. time and indicating the balloon pressure supplied during steps of the crimping process.

FIGS. 1A-1B describe a flow process and graph, respectively, of a crimping method for a 3.5 mm diameter and 18 mm length scaffold (FIGS. 1A-1B are taken from the '225 application). The method is described in terms of a series of five "stages" with diameter reduction steps between stages. Each "stage" refers to a period where the crimper jaws are maintained at a constant diameter for a dwell period. The scaffold diameter is held constant during these periods. The boxes 20 and 10 in the graph is identifying times when the iris diameter is being reduced (same convention used for FIGS. 4B and 5B, supra).

For the stages preceding the "final alignment" or "verify final alignment" step in FIGS. 1A-1B, where the scaffold and balloon are removed from the crimper to check alignment, the balloon is inflated to minimize further out of plane, or irregular movement or twisting of struts initiated in preceding crimping steps during subsequent crimping steps. Some of the advantages of inflating a balloon during these dwell periods to achieve this result are explained in U.S. application Ser. No. 12/861,719 filed Aug. 23, 2010 (US20120042501) (the '719 application).

As mentioned earlier, a polymer scaffold, and in particular a misaligned polymer scaffold is more susceptible to damage within a crimper than a corresponding metal stent. A polymer scaffold that has even a "slight" misalignment within the crimper has a far greater chance of becoming damaged than a metal stent. Of course, the need to avoid twisting or bending in struts of metal stents when in a crimper is known. However, unlike metal stents, which are far more tolerant of local irregular or non-uniform forces acting on struts through blade edges, polymer struts are more easily distorted when the crimping forces are non-uniformly applied. Due to the proximity of struts to each other (as required since thicker and wider struts are needed to provide equivalent stiffness to a metal stent and there is sometimes a greater diameter reduction needed during crimping), there is a greater chance of abutting struts which leads to out of plane twisting and overlapping scaffold structure in the crimped state. The effects of irregular or non-uniform crimping forces on a polymer scaffold are therefore more severe than in the case of a metal stent. The differences are most clearly evident in the instances of cracking and/or fracture in deployed polymer scaffolds that show irregular twisting or bending.

More local support for individual struts during the dwell periods is believed to correct for struts predisposed to twist or overlap with adjacent struts (a strut predisposed to twist or overlap with other struts refers to a strut that was previously slightly bent or twisted out of plane when the scaffold was at a larger diameter). In essence, balloon pressure during the dwell periods is believed to apply a beneficial correcting force on the luminal side of struts, which can serve to limit a strut's potential to overlap or twist further as crimper blades are applied in subsequent steps.

When crimped down from a larger diameter (e.g., from 0.136 to 0.11 in in FIG. 1A), there is little stabilizing support available for the scaffold since its diameter is much larger than the deflated balloon upon which the scaffold sits. As such, any initial non-uniform applied crimping force, or misalignment, e.g., due to a residual static charge on the polymer surface, can initiate irregular bending that becomes more pronounced when the scaffold diameter is reduced further. Friction between the blades and the scaffold surface, or residual static charge or static charge buildup induced by sliding polymer surfaces are also suspect causes of this irregular deformation of the scaffold. When the balloon is inflated to support the scaffold from the interior during dwell periods, the irregular bending and twisting of struts seen at the final crimp diameter (when the scaffold is removed from the crimper) were reduced substantially. The scaffold was more able to maintain a proper orientation with respective to the crimper axis.

Referring again to FIGS. 1A-1B, the scaffold is partially crimped, then removed from the crimper to check its alignment on the balloon (Stages I, II, III as the dwell periods). The scaffold is then returned to the crimper to perform final crimp steps, e.g., Stage IV, reduce to 0.044 in, then dwell Stage V. During these final steps the balloon is approximately at a constant pressure. Unlike earlier crimping steps, the balloon is pressurized when the scaffold is crimped to the final diameter. The presence of balloon pressure during the final crimp (the "intermediate pressure" step), as compared to the same process without the "intermediate pressure" step, i.e., about atmospheric balloon pressure for the final crimp, greatly increased the retention force of the scaffold to the balloon. Stated differently, the retention force of scaffold to balloon was much higher when the balloon is pressurized during the final crimp, or diameter reduction step.

It is believed that the greatly increased retention force was achieved because the balloon material opposing gaps in scaffold struts during the final crimp tended to extend in-between gaps more often as the scaffold was crimped due to the opposing balloon pressure applied to the balloon material. Without this pressure, the balloon material tended to deflect away from the gaps as the size of the gaps narrowed during the final crimp. Essentially, the balloon pressure forced more balloon material into gaps—rather than deflect the material away from the gaps—when the diameter is being reduced in size.

It should be noted that there was concern over whether the "intermediate pressure" step would cause balloon damage for balloon pressure applied in an amount that would make a difference in scaffold retention. The gaps between scaffold struts for a scaffold having significant diameter reductions and relatively thick struts are narrower than for struts of a metal stent. Forcing balloon material into narrower spaces gave rise to concerns that balloon material would be excessively pinched between struts, thereby causing damage to the balloon. In one example the pressure applied during the earlier dwell periods (Stages I, II and III) is about twice that applied during the final crimp steps (150 psi and 70 psi, respectively), as shown in FIGS. 1A-1B. This ratio of balloon pressure (i.e. about 150:70 for corresponding diameters of about 0.1 in and about 0.07 in, about 3.5 mm pre-crimp diameter and about 0.044 in final crimp diameter, FIGS. 1A-1B) was found to produce good results, despite the previous concerns. It is contemplated that other pressure ratios, or increased pressure values may improve results. It was found, however, that a relatively modest amount of pressure applied during the intermediate pressure step can produce significant improvement in scaffold retention, so that the risk of damaging a balloon and/or scaffold is reduced.

According to the '225 application, balloon pressure may be applied in bursts, rather than set at a constant level, during the intermediate pressure step. Further, there may be benefits to using balloon pressure during the prior partial crimp steps. Since the scaffold is re-aligned following the earlier crimp steps, the benefits of using balloon pressure during earlier crimping steps are not so much believed to lay in increased retention. Rather, balloon pressure may help avoid irregular twisting or bending in scaffold struts (for the reasons discussed above) as the scaffold diameter is being reduced.

EXAMPLE 1

Figure 8A:
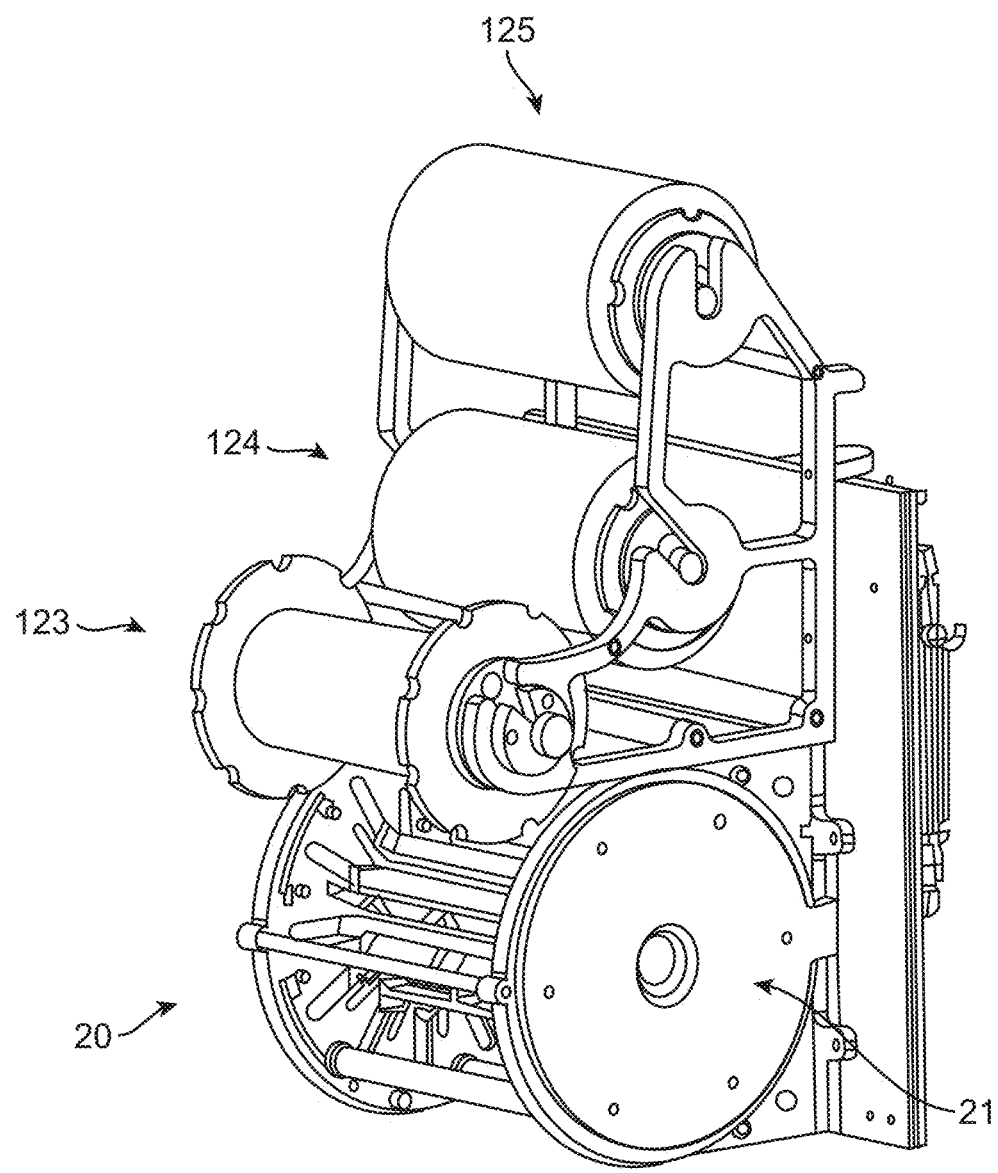
FIG. 8A is a perspective view of a prior art film-headed crimper.
Figure 8B:
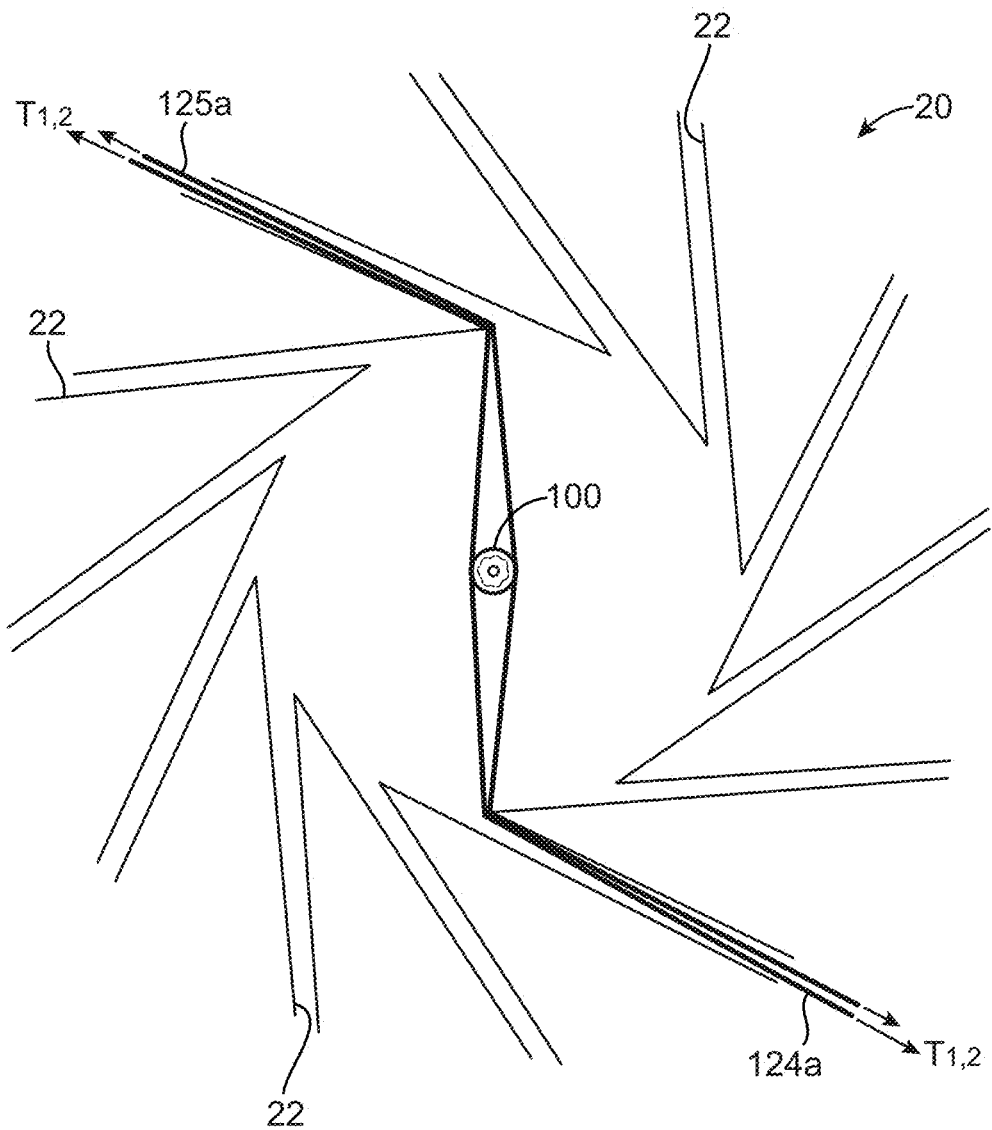
FIG. 8B is a frontal view of the head of the film-headed crimper of FIG. 8A as crimper jaws are being brought down on a stent.

Further details of the FIG. 1A flow process for a 3.5 mm scaffold manufacture and crimping to a delivery balloon will now be discussed. FIG. 1B illustrates in graphical form the crimping portion of the FIG. 1A flow—a graph of scaffold diameter verses time with a balloon pressure of 150 psi or 70 psi applied during the dwell periods and the intermediate pressure step (i.e., crimping between Stage IV and Stage V). The scaffold was crimped using a crimper having film-sheets disposed between the metal crimper blades and the scaffold. This particular type of crimper was discussed earlier in connection with FIGS. 8A-8B.

As discussed above, the scaffold is formed from a PLLA or PLGA precursor, including a biaxial expansion of the precursor to form a tube, followed by laser cutting the scaffold from the tube. Next, a pre-crimp procedure is performed, which includes placing the scaffold between the balloon markers and aligning the scaffold with the iris of the crimper. Using an anti-static air gun, both the scaffold and interior of the iris chamber are deionized. The deionization step was found necessary to reduce misalignments of the scaffold resulting from a static charge buildup caused by sliding contact between polymer surfaces, as explained in more detail in U.S. application Ser. No. 12/776,317 filed May 7, 2010.

Stage I:

The scaffold (supported on the balloon of the balloon-catheter) is placed within the crimp head. The crimping temperature is obtained by heating the crimper jaws to an appropriate temperature and then bringing the jaws into thermal contact with the scaffold. The crimper jaws are set to 0.136 in and maintained in this position for about 10 seconds to allow the scaffold temperature to increase to a crimping temperature that is near to, but below the TG of the scaffold material (e.g., the crimping temperature for a PLLA scaffold of FIG. 1 is 48+/−3° C.). More generally, the scaffold temperature may be between 5 and 15 degrees Celsius below TG for the polymer material. Whenever the scaffold is within the crimper head its temperature is at, or rose to the crimping temperature (e.g., 48+/−3° C.) for the crimping process described in FIGS. 1A-1B.

After the scaffold reaches the crimping temperature, the iris of the crimper closes to reduce the scaffold diameter from 0.136 in (3.5 mm) to about 0.11 in, or about a 20% diameter reduction. During this diameter reduction step (Stage I→Stage II) the balloon pressure is maintained at about atmospheric temperature. The about 20% reduction in diameter occurs over a period of about 5.2 seconds. As compared to subsequent diameter reduction steps, this diameter reduction is performed more slowly because strut angles are at their widest. It was found that a slow rate of diameter reduction can significantly improve yield, in terms of more uniformity of compression in the scaffold structure; that is, to enable the scaffold structure to compress more evenly, without irregular bending or twisting of strut and/or link structure. Further details on this aspect of the crimping process are described in the '719 application.

Stage II:

The crimper jaws are held at the 0.11 in diameter, the balloon is inflated to a pressure of 150 psi, and the scaffold and balloon are maintained in this configuration for a 30 second dwell period at the crimping temperature. As explained earlier, the balloon is inflated to 150 psi to help with stabilizing the scaffold structure and correcting for any misalignment, or twisting of struts that might have occurred when the iris diameter was being reduced in size.

After the 30 second dwell period is complete, the balloon pressure is returned to about atmospheric pressure and the crimper iris is moved from 0.11 in to 0.068 in or about a 38% diameter reduction. During this second diameter reduction or crimp step (Stage II→Stage III) the balloon pressure is maintained at about ambient temperature. This about 38% reduction in diameter occurs over a period of 1.0 second. The about 50% diameter reduction was found to achieve an acceptable balance between balloon-scaffold engagements while retaining an ability to re-align the scaffold in a Final Alignment step). If the scaffold is crimped too tightly before Final Alignment, then it becomes difficult to re-position it between balloon markers. If crimped too loosely before Final Alignment, then the scaffold can shift again after Final Alignment. It will be appreciated that this balance also should take into consideration the available spacing between struts for balloon material.

Stage III:

The crimper jaws are held at the 0.068 in diameter, the balloon is again inflated to a pressure of 150 psi, and the scaffold and balloon maintained in this configuration for a 15 second dwell period at the crimping temperature to correct or counter any twisting or misalignment that might have developed when the scaffold diameter was reduced by about an additional 38%.

Final Alignment Step:

After the 15 second dwell period is complete, the scaffold and balloon are removed from the crimper to check the scaffold alignment on the balloon. This alignment involves a visual inspection and if necessary manual adjustment of the scaffold to place it between the balloon markers. Alternatively, alignment may be performed by an automated process, as explained in U.S. application Ser. No. 12/831,878 filed Jul. 7, 2010.

As mentioned earlier, the scaffold's starting or pre-crimp diameter is about equal to, or greater than the deployed diameter for the scaffold, which is between about 2.5 and 3.0 times its final crimped diameter. The expanded tube and pre-crimp scaffold diameter is 2.93 times the final-crimp size in the illustrated example. This difference in diameters between scaffold and balloon, coupled with the likelihood that crimper jaws will not apply a net-zero longitudinal force on the scaffold as the diameter is reduced, and/or that the scaffold will be slightly misaligned when it reaches the balloon surfaces, has lead to a need for re-aligning, or verifying alignment of the scaffold on the balloon; that is, checking to see that the scaffold is located between balloon markers.

The additional, time-consuming alignment step that interrupts the crimping process is typically not required for a metal stent, for two reasons. First, the starting diameter for a metal stent is much closer to the final diameter, which means the balloon-stent interaction that holds the stent in place happens relatively quickly. Second, for higher crimping rates used for metal stents, there is usually less ability for the stent to shift longitudinally over the balloon surface. Metal stents can be crimped at relatively high rates, whereas crimp rates for polymer scaffolds generally should be monitored and often times reduced (from metal crimp rates) because a polymer scaffold's structural integrity in its crimped and deployed states is affected by the crimp rate. While metals exhibit rate independent material behavior, polymers are viscoelastic and exhibit rate dependent material response. Polymers subjected to higher strain or displacement rates will tend to experience higher stresses and exhibit less ductility.

After Stage III the scaffold's diameter has been reduced to about ½ of its starting diameter. In some cases not until a scaffold diameter is reduced to about 50% of its pre-crimp diameter size is the scaffold-balloon interaction sufficient to prevent longitudinal shifting of the scaffold on the balloon when the scaffold is crimped down further. In the example of FIG. 1A the final-alignment step is performed once the scaffold reaches about 50% of its pre-crimp diameter.

Stage IV:

The scaffold and balloon are placed into the crimper. The jaws are closed to a diameter of 0.07 in and the balloon inflated to a pressure of 70 psi (the pressure used for the intermediate pressure step in this example). Thereafter the scaffold is crimped to its final crimp diameter of 0.044 in or about a 33% reduction in diameter over a period of about 2.6 seconds while balloon pressure is maintained at 70 psi. Before the final diameter reduction to 0.044 in commences, a dwell period of 10 seconds at the 70 psi balloon pressure is performed to allow time for the scaffold to return to the crimping temperature.

As illustrated in FIG. 1B, at the start of the Stage IV step the balloon pressure is set to 70 psi, and this setting is unchanged during the subsequent Stage IV dwell, the subsequent diameter reduction from 0.07 in to 0.044 in or about a 33% reduction ("intermediate pressure"), and the Stage V dwell. The pressure is not adjusted to maintain 70 psi; as such the balloon pressure is expected to change somewhat from 70 psi during the intermediate pressure step.

Stage V:

After the scaffold has been reduced in diameter from 0.07 in to 0.044 in the balloon pressure is maintained at 70 psi for a period of about 15 seconds.

Following Stage V dwell period, the balloon pressure is returned to about atmospheric pressure and the crimper jaws are held at the final crimp diameter for a 185 second dwell period. During this final dwell period the degree of recoil in the scaffold is reduced. Immediately following the 185 second dwell the scaffold is removed and a retaining sheath is placed over the scaffold to reduce recoil.

Figure 7:
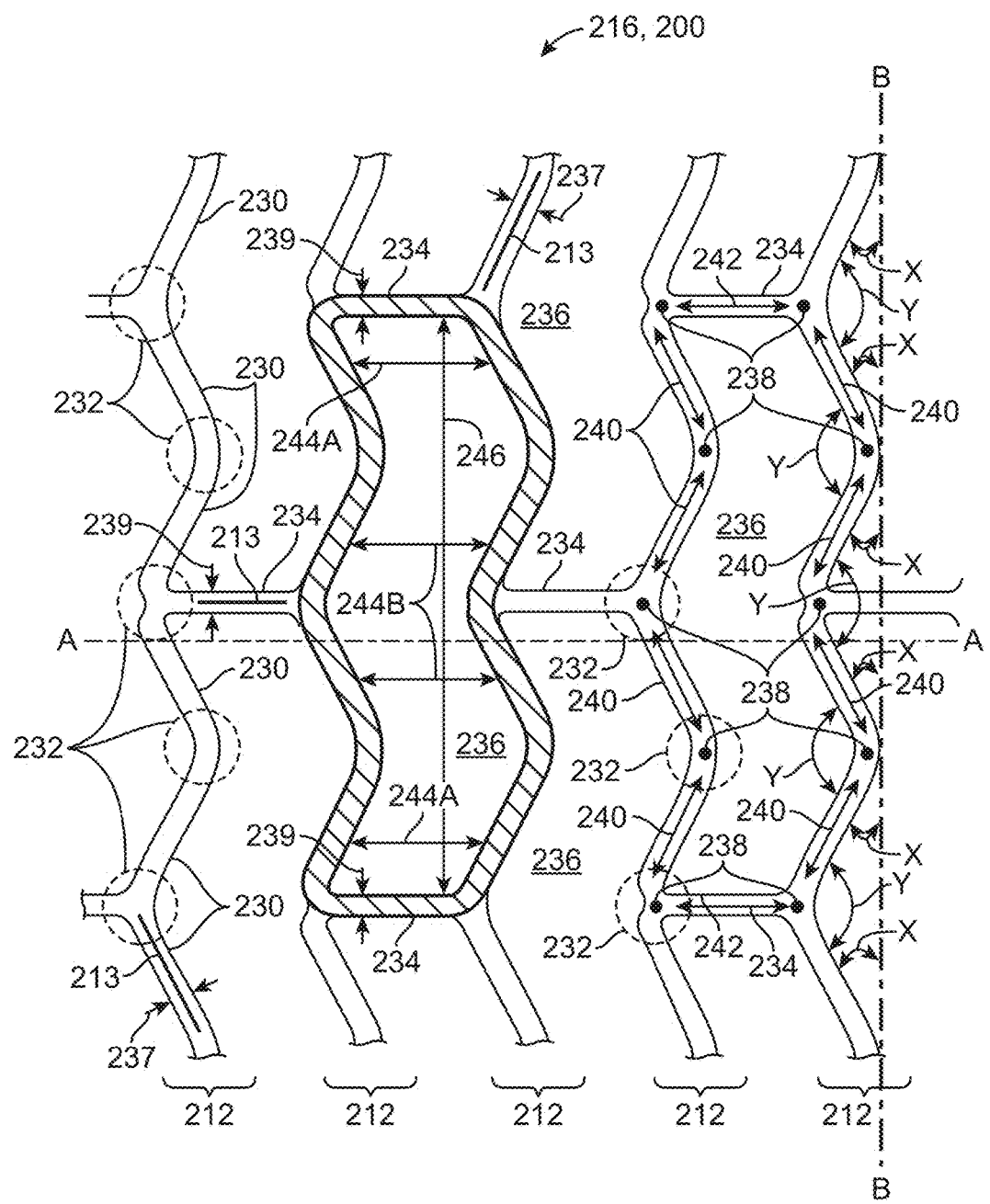
FIG. 7 shows an example of a portion of a scaffold for crimping to a balloon according to the disclosure.

Trials were conducted and reported in the '225 application (reproduced below) to estimate the likely pull-off or retention force for a 3.5 mm×18 mm PLLA scaffold crimped to a 0.044 in final crimp diameter and crimped to a PEBAX balloon. The TABLE below shows results from these trials. The mean of the retention force for the scaffold for 9 trials using the process of FIGS. 1A-1B was significantly higher than the mean of the retention force for the "control case"— i.e., the same process as in FIGS. 1A-1B but without balloon pressure when the diameter was reduced from 0.07 in to 0.044 in the final crimping stages. The scaffolds used during these trials had substantially the same pattern as shown in FIG. 7. Statistics are shown below for five Test cases.

|  | Crimping process | Mean retention force (lb) | Standard deviation (lb) |
| --- | --- | --- | --- |
| FIG. 1A process | Test case 1 | 1.32 | 0.33 |
|  | Test case 2 | 1.63 | 0.11 |
|  | Test case 3 | 1.43 | 0.16 |
|  | Test case 4 | 1.56 | 0.17 |
|  | Test case 5 | 1.55 | 0.12 |
| FIG. 1A process without balloon pressure when diameter reduced from .07 to .044. | Control: | 0.70 | 0.10 |

The results above were unexpected, since it was previously not believed that a pressurization of the balloon during the final crimp by about ½ the pressure of prior dwell periods would make much of a difference in the retention force. The results demonstrate an about 30% to about 88% improvement in retention force over the "control" case.

EXAMPLE 2

The process described in FIGS. 1A-1B had been adopted in a modified form for use in crimping a scaffold intended for use in a peripheral artery, e.g., a scaffold described in co-pending application Ser. No. 13/015,474. When applied to this peripheral scaffold, however, it was found that the scaffold exhibited non-uniform expansion characteristics. In order to address this problem, a modified crimping process was devised. Such a process is described in co-pending application Ser. No. 13/194,162 ('162 application), which has a common assignee to the present application. The process proposed is summarized in TABLE 1.

TABLE 1

Crimping process described in the '162 application

| Crimp Control settings | Outer Diameter setting (in.) | Crimp head Speed (in/sec) | Dwell times (sec) | Balloon pressurization (50 psi) | Balloon pressurization dwell times (sec) |
| --- | --- | --- | --- | --- | --- |
| Initial point | 0.640 |  |  |  |  |
| Step 1 | 0.354 | 0.300 | 0 | Ambient | 0 |
| Step 2 | 0.270 | 0.005 | 30 | Ambient | 0 |
| Step 3 | 0.210 | 0.005 | 30 | Ambient | 0 |
| Step 4 | 0.160 | 0.005 | 30 | Ambient | 0 |
| Step 5 | 0.130 | 0.005 | 30 | Ambient | 0 |
| Step 6 | 0.140 | 0.050 | 30 | Ambient | 0 |
| Step 7 | 0.130 | 0.005 | 30 | Ambient | 0 |
| Step 8 | 0.100 | 0.005 | 30 | Pressure | 30 |
| Step 9 | 0.062 | 0.005 | 30 | Ambient | 170 |

As compared to the process depicted in FIGS. 1A-1B (as modified for use with a peripheral scaffold), balloon pressure is applied only during the final crimping step. Prior to this step the balloon was not pressurized. By not pressurizing the balloon during steps 5 and 7, it was found that the balloon retained, more or less, its original balloon folds, as compared to the asymmetric or non-uniform arrangement of balloon folds present about the balloon's circumference when the balloon was also pressurized during dwell periods (steps 5 and 7) as explained below in connection with FIGS. 2A-2C. According to the '162 application, when balloon pressure is applied according to the TABLE 1 process, a substantial improvement in uniformity of expansion can be achieved for a balloon-expanded scaffold.

While the uniform-expansion results reported in the '162 application are encouraging, it should be noted that, unlike a coronary scaffold, processes for crimping a peripheral scaffold generally produce adequate stent retention forces without additional measures being needed in order to assure that the scaffold will remain on the balloon when the scaffold is advanced through tortuous vessels. The same cannot be said for a coronary scaffold.

A peripheral scaffold is typically much longer than a coronary scaffold (retention force is proportional to the length of a scaffold). Thus, while a relatively low retention force per unit length may be acceptable for a peripheral scaffold, the same retention force per unit length may not be acceptable for a coronary scaffold. There is, therefore, a need for a crimping process for a coronary scaffold that both increases the retention force per unit length and results in more uniform expansion of the coronary scaffold.

Returning again to FIGS. 1A-1B, this process when applied to a coronary scaffold having a length of 18 mm (typical size for a coronary scaffold) increased the retention force over prior methods of crimping, as noted earlier. Also discussed earlier, the balloon is inflated only after the scaffold is partially crimped, and balloon pressure is applied only during dwell times and during a final crimp step (i.e., the "intermediate pressure step").

In a preferred embodiment the balloon is inflated, or at least partially inflated before the scaffold diameter is reduced within the crimper. Additionally, balloon pressure is maintained for substantially the entire crimp process, as opposed to only during a portion of the crimping time, as was the case of the FIGS. 1A-1B examples. The balloon pressure may be maintained at more or less a constant value as in the examples (below) or varied depending on the crimped state of the scaffold. For example, the balloon inflation may begin at 150 psi then be reduced as the scaffold is crimped down, e.g., reduced from 150 psi to 70 psi, or from 150 to between 20-70 psi, or from 70 to 20 psi after the crimper iris has reached a pre-designated diameter. In other embodiments, the ratio of balloon pressure when the iris has a first diameter, e.g., pre-crimp diameter, to a second diameter, e.g., just prior to the final crimp, may be about 7:1 or about 2:1 for a corresponding about 3:1 to 2:1 iris diameter (e.g., the balloon pressure is about 7/2 times greater for an iris diameter prior to crimping (Stage I) then the balloon pressure for the iris diameter just prior to the final crimp).

Continuously maintaining an inflated, or partially inflated balloon, or gradually reducing the inflation pressure during most of the crimping process is presently preferred based on a finding that an inflated balloon promotes a more uniform expansion of the scaffold from its crimped to deployed configuration. It is further believed that by maintaining balloon pressure during the crimping process one can even produce a higher retention force. These discoveries and/or insights are based on inspection of expanded scaffolds and balloon cross-sections for scaffolds crimped using the FIGS. 1A-1B process.

Figure 2A:
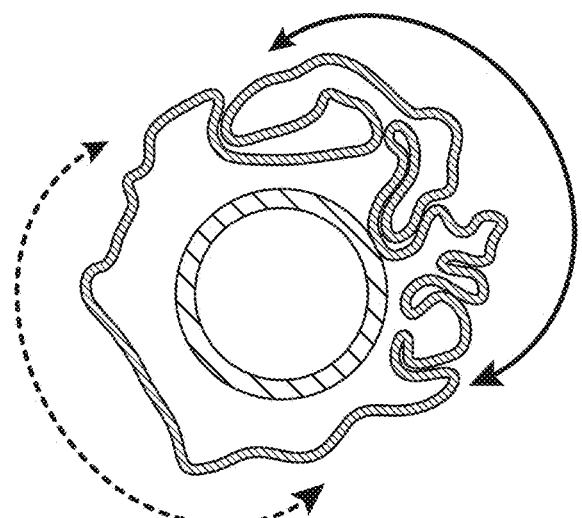
FIG. 2A shows an arrangement of balloon folds about a catheter shaft and near a distal end of a balloon after completion of the crimping process of FIGS. 1A-1B (crimped scaffold not shown).
Figure 2B:
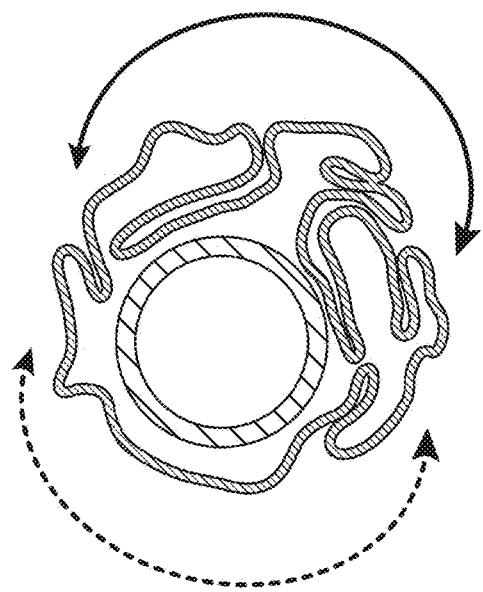
FIG. 2B shows an arrangement of balloon folds about a catheter shaft and near the middle of the balloon after completion of the crimping process of FIGS. 1A-1B (crimped scaffold not shown).
Figure 2C:
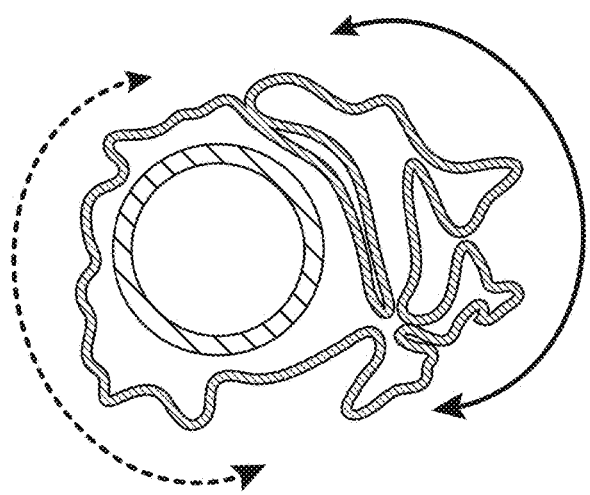
FIG. 2C shows an arrangement of balloon folds about a catheter shaft and near the proximal end of the balloon after completion of the crimping process of FIGS. 1A-1B (crimped scaffold not shown).

FIGS. 2A, 2B, and 2C are drawings intending to depict observed arrangements, or distributions of balloon folds when a scaffold is fully crimped using the process of FIGS. 1A-1B. Shown in FIGS. 2A, 2B, and 2C is a catheter shaft 4 and the balloon 8 (the crimped scaffold is not also drawn so that the balloon shapes can be more easily shown in drawings). FIG. 2A shows the arrangement of balloon folds about the circumference of the catheter shaft nearer the distal end of the balloon. FIG. 2B shows the arrangement of balloon folds about the circumference of the catheter shaft nearer the middle of the balloon. And FIG. 2C shows the arrangement of balloon folds about the circumference of the catheter shaft nearer the proximal end of the balloon (photographs of the cross-section of a scaffold crimped to a balloon, taken from the distal, middle and proximal portions of the balloon are provided in FIGS. 9A-9C).

Figure 3:
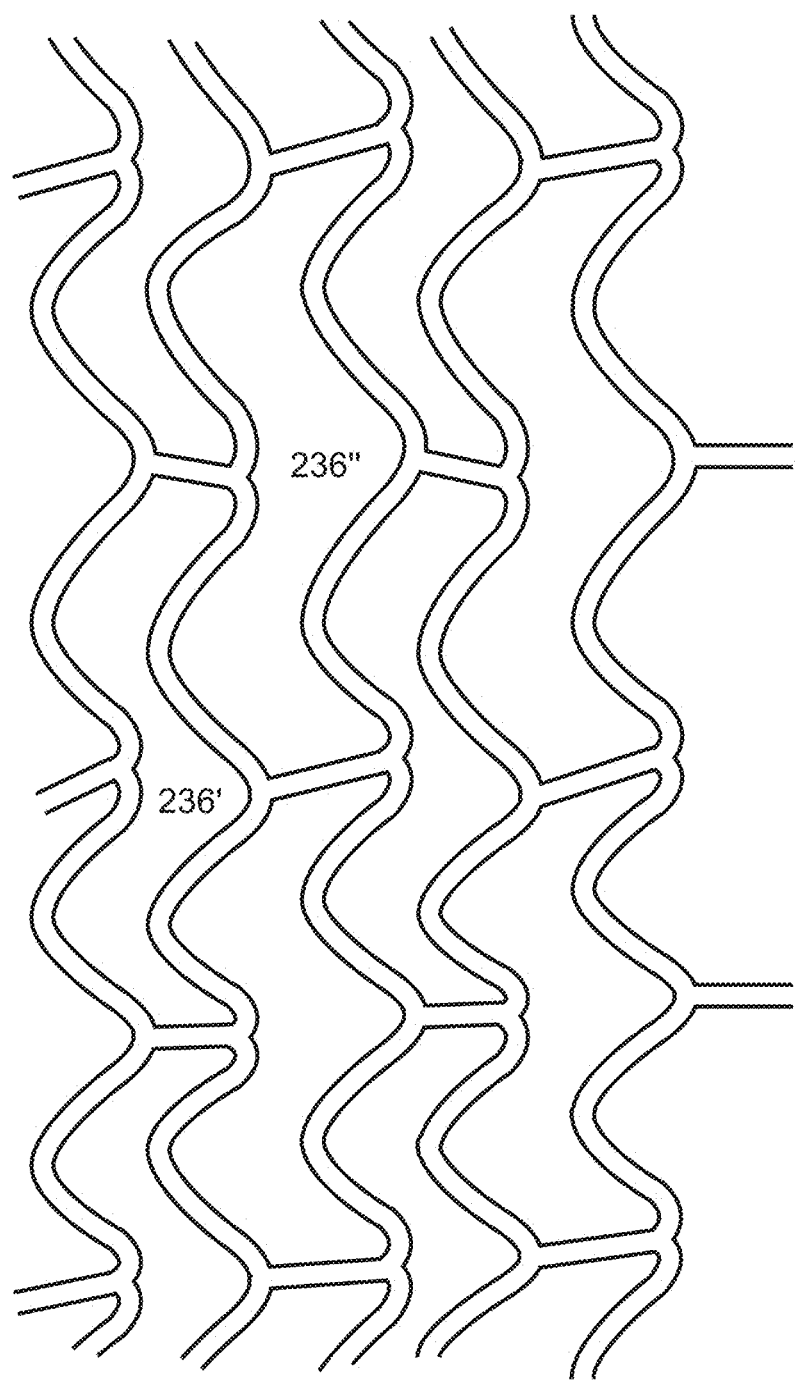
FIG. 3 shows a portion of a scaffold after balloon expansion for a scaffold crimped to a balloon using the crimping process of FIGS. 1A-1B.
Figure 13A:
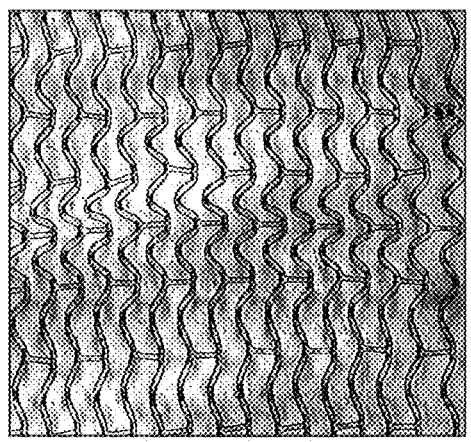
FIG. 13A is a FINESCAN image of a scaffold having a pattern similar to that shown in FIG. 7. The scaffold was crimped using the process of FIGS. 1A-1B. The scaffold was then expanded by inflation of the balloon. As shown in this image, the scaffold exhibits a non-uniform expansion.

As shown in each of these three drawings or photographs, about half of the circumference of the catheter shaft 4 is traversed by only a single, unfolded layer of balloon material. The remaining half of the shaft circumference has several balloon folds bunched together. When pressure is applied to a balloon having folds arranged in this manner and engaged with a crimped stent, the resulting balloon expansion will impart higher expansion forces on the scaffold struts abutting the balloon folds bunched within region A' than the struts abutting the balloon material extending over section B'. The result is a non-uniform expanded scaffold pattern, as depicted in FIG. 3 (FIG. 13A is a FINESCAN image of an expanded scaffold after crimping using the FIGS. 1A-1B process). FIG. 10 shows an expanded scaffold. This scaffold was crimped using the process of FIGS. 1A-1B then expanded by the balloon. The scaffold shows a non-uniform expansion of rings and there are fractured struts.

When comparing FIG. 3 to FIG. 7 (idealized scaffold pattern after expansion), the effects of a non-uniform arrangement of balloon folds becomes apparent. The shapes of the cell regions, e.g., 236' and 236", are irregular. These irregular-shaped cells indicate that some rings have been expanded beyond their design angles while others have not been expanded to their design angles. The over-extended angles can lead to crack propagation at the crown and in some cases, failure of rings at or near the crown. While the net result is the intended expanded diameter, e.g., about 3.5 mm, the distribution of stresses among the ring struts is uneven and affects the structural integrity of the expanded scaffold.

Examples of preferred embodiments for a crimping process are now provided. Two examples are provided. For each example, several of the same processes described earlier for FIGS. 1A-1B also apply, except where noted. Therefore, unless stated otherwise, the same description above for FIGS. 1A-1B also applies to these examples.

EXAMPLE 3

Figure 4A:
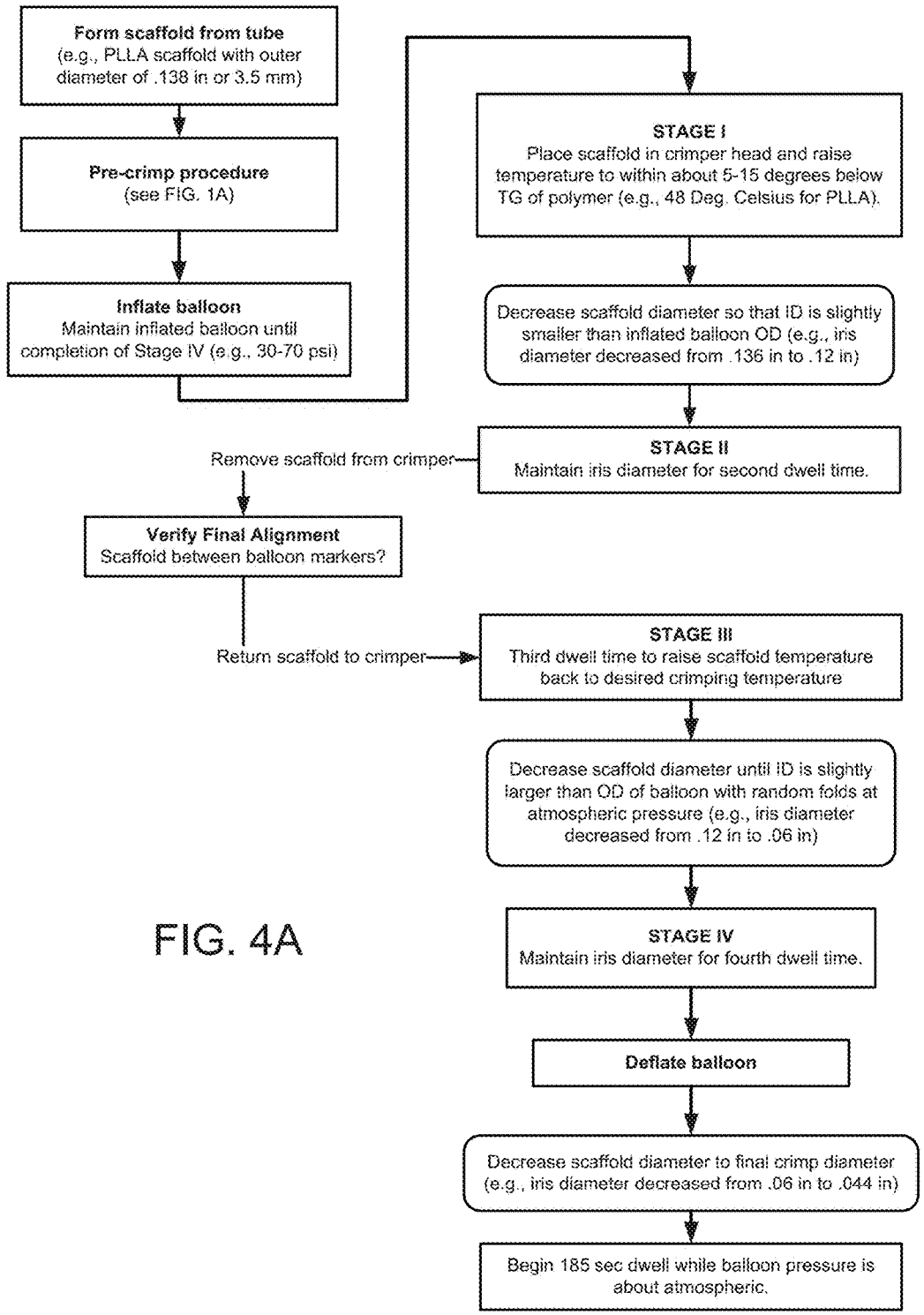
FIG. 4A is another example of a flow process for crimping a polymer scaffold to a balloon.
Figure 4B:
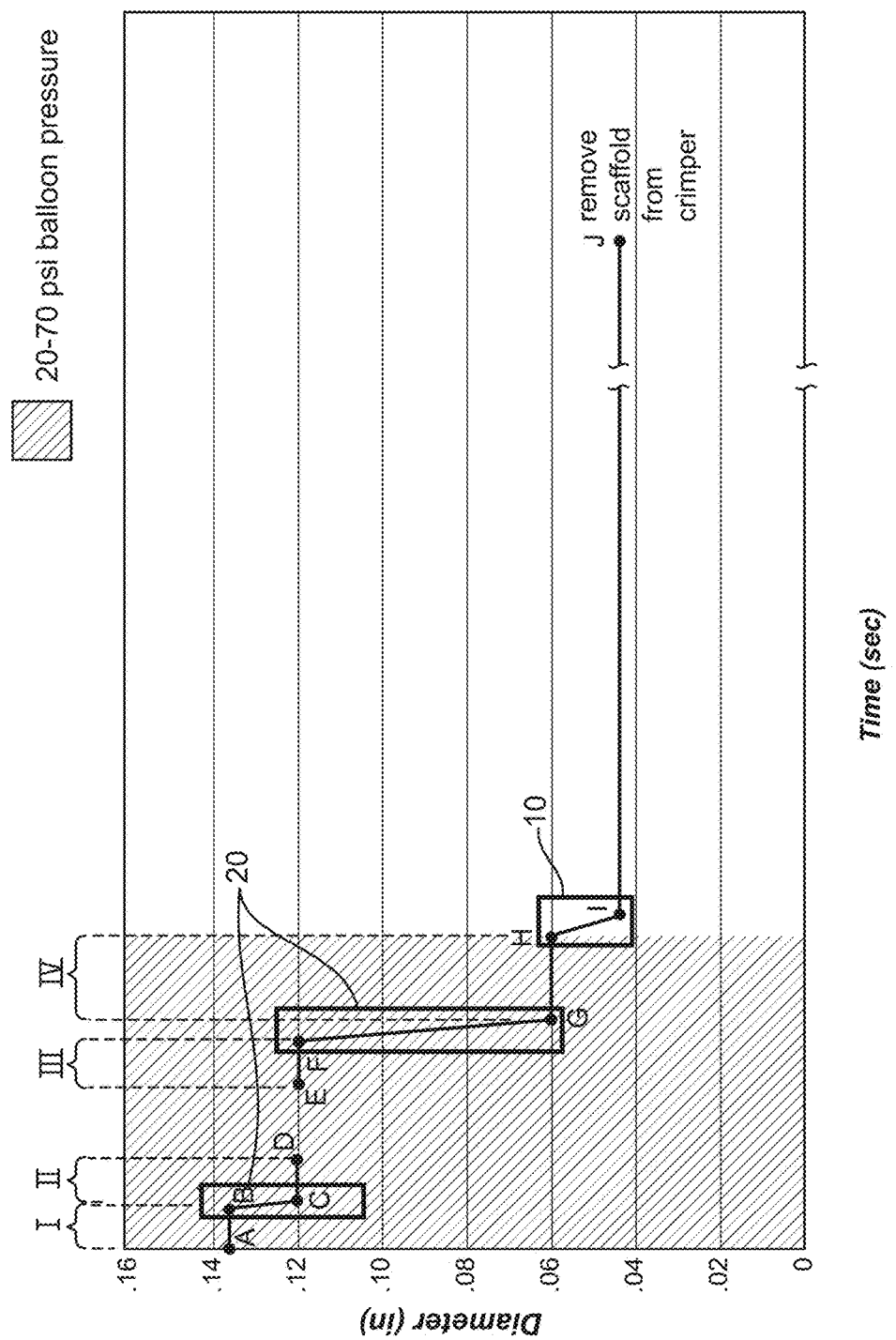
FIG. 4B shows the crimping portion of the FIG. 4A flow process in graphical form, plotting scaffold diameter vs. time and indicating the balloon pressure supplied during steps of the crimping process.

FIGS. 4A-4B illustrate the steps associated with a first example of a crimping process according to the preferred embodiments. FIG. 4B illustrates in graphical form the crimping portion of the FIG. 4A flow—a graph of scaffold diameter verses time with a balloon pressure of between about 20-70 psi applied throughout substantially all of the crimping process. For example, the balloon pressure is maintained at between 20-70 psi until the completion of a Stage IV of a preferred crimping process.

Stage I:

The scaffold supported on the inflated balloon of the balloon-catheter is placed within the crimp head. The balloon when inflated and supporting the scaffold in this state preferably has substantially all folds removed.

After the scaffold reaches the crimping temperature, the iris of the crimper closes to reduce the scaffold inner diameter (ID) is slightly less than the outer diameter (OD) of the pressurized balloon (e.g., from 0.136 in (3.5 mm) to about 0.12 in, or about a 15% diameter reduction).

Stage II:

The crimper jaws are held at the 0.12 in diameter and maintained at this diameter for a second dwell period at the crimping temperature.

Final Alignment Step:

After the second dwell period is complete, the scaffold and balloon are removed from the crimper to check the scaffold alignment on the balloon.

After Stage II the scaffold's diameter has been reduced to about 80-85% of its starting diameter. It was observed that when the scaffold diameter is reduced to about 80-85% of its pre-crimp diameter size the scaffold-balloon interaction is sufficient to prevent longitudinal shifting of the scaffold on the pressurized balloon when the scaffold was crimped down further. In the example of FIGS. 4A-4B, therefore, the final-alignment step is performed once the scaffold reaches about 80-85% of its pre-crimp diameter for the balloon, which is preferably inflated to less than its fully inflated configuration, e.g., 20-70 psi. The balloon inflation pressure for crimping according to the disclosure may be expressed as a percentage of the nominal inflation pressure for the balloon, e.g., 7 atmospheres (atm) for a 3.0 mm balloon. Thus, for the inflation pressure 20-70 psi in the examples and a 7 atm nominal inflation pressure the crimping balloon pressure would correspond to about 20% to about 80% of the nominal inflation pressure for the balloon. And for the balloon having an 18 atm upper or over-inflated pressure (about 3.5 mm for a 3.0 mm nominally inflated balloon) the crimping balloon pressure would correspond to about 10% to about 30% of the upper or over-inflated balloon pressure.

Stage III:

The scaffold and balloon are returned to the crimper. The jaws are closed to a diameter the same as or similar to what is set in stage II, which may be slightly less than the scaffold OD when it is removed from the crimper (to check alignment) and recoils slightly. The crimper jaws are held at this diameter for a third dwell time, which may be the time needed for the scaffold to return to the crimping temperature.

The iris diameter is then reduced to an ID corresponding to about the OD for the balloon if the balloon were not pressurized and had randomly distributed folds. That is, the scaffold is crimped down to the approximate OD for the balloon if it were pressurized then deflated so that substantially all pre-made folds are replaced by random folds. For example, the iris diameter is reduced down to about 0.06 in for the 3.5 mm scaffold where about 0.06 in corresponds approximately to the OD of the balloon at atmospheric pressure after the balloon is inflated and then deflated so that substantially all folds are removed. After this diameter reduction the scaffold OD is about 50% of its diameter at Stage III and about 40% of its starting, or pre-crimp OD.

Stage IV:

After the scaffold OD is reduced to about 40% of its starting diameter, the crimper jaws are held at this diameter for a third dwell time.

Following the Stage IV dwell period, the balloon is deflated or allowed to return to atmospheric pressure and the iris of the crimper is reduced down to a final crimp OD, e.g., 0.044 in or about 30% of its pre-crimp OD. This balloon deflation may occur by opening the valve supplying the pressurized gas to the balloon while, or just before the iris diameter is reduced to the final crimp diameter.

The crimper jaws are then held at the final crimp diameter for about a 165 second dwell period. This final dwell period is intended to reduce the amount of scaffold recoil when the crimped scaffold is removed from the crimper. Immediately following the 165 second dwell the scaffold is removed and a retaining sheath is placed over the scaffold to further aid in reducing recoil. A leak test may be done after the final stage crimping.

The foregoing example of a preferred crimping process, which pressurizes the balloon through most of the crimping steps (e.g., up until the final crimp step) is expected to provide two benefits. The first benefit is increased scaffold-balloon retention. By maintaining pressure in the balloon through most of the crimping steps, more balloon material should become disposed between struts of the scaffold since balloon material is being pressed more into the scaffold, especially when the spaces between struts are at their largest, e.g., the diameter reduction between Stages I and II, than the case when crimping is done without balloon pressurization, or only after the scaffold is reduced in diameter. Additionally, it is expected that by substantially removing folds before any diameter reduction, the balloon material becomes more compliant. As such, more balloon material is able extend between struts, rather than being pressed between the scaffold and catheter shaft when the scaffold is being crimped.

The second benefit of balloon pressurization is more uniform expansion of the crimped scaffold when the balloon is expanded. When the balloon is inflated from the beginning, before any crimping takes place and when there is the greatest space available for the balloon to unfold within the mounted scaffold, balloon material become more uniformly disposed about the circumference of the catheter shaft after crimping. If the balloon is only partially expanded, as in the case where the balloon is inflated after the scaffold has been partially crimped (thereby leaving less space available for the balloon to fully unfold), it is believed that the presence of folds or partial folds causes balloon material to shift or displace during crimping, thereby resulting in a more non-uniform distribution of balloon material about the circumference of the catheter shaft after crimping. This type of behavior is depicted in FIGS. 2A-2C.

Figure 6A:
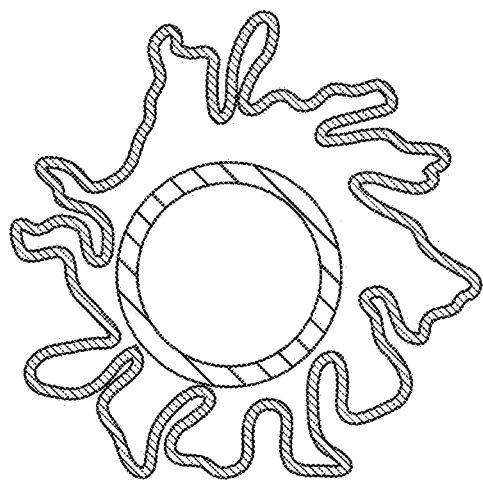
FIG. 6A shows an arrangement of balloon folds about a catheter shaft and near a distal end of a balloon after completion of the crimping process of FIGS. 4A-4B (crimped scaffold not shown).
Figure 6B:
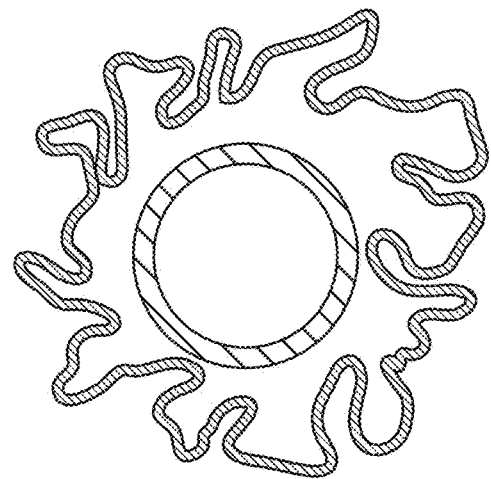
FIG. 6B shows an arrangement of balloon folds about a catheter shaft and near the middle of the balloon after completion of the crimping process of FIGS. 4A-4B (crimped scaffold not shown).
Figure 6C:
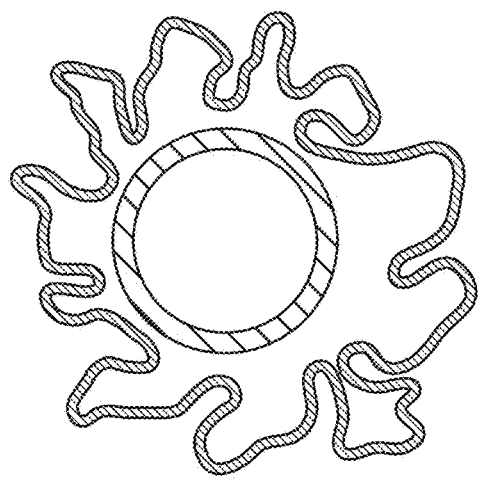
FIG. 6C shows an arrangement of balloon folds about a catheter shaft and near the proximal end of the balloon after completion of the crimping process of FIGS. 4A-4B (crimped scaffold not shown).

FIGS. 6A, 6B, and 6C are drawings intending to depict observed arrangements, or distributions of balloon folds when a scaffold is fully crimped (scaffold not shown) using the preferred process of FIGS. 4A-4B ((photographs of the cross-section of a scaffold crimped to a balloon, taken from the distal, middle and proximal portions of the balloon are provided in FIGS. 11A-11C). FIG. 6A shows the arrangement of balloon folds about the circumference of the catheter shaft nearer the distal end of the balloon. FIG. 6B shows the arrangement of balloon folds about the circumference of the catheter shaft nearer the middle of the balloon. And FIG. 6C shows the arrangement of balloon folds about the circumference of the catheter shaft nearer the proximal end of the balloon. As compared to the corresponding FIGS. 2A, 2B and 2C discussed earlier, FIGS. 6A-6C shown balloon material more evenly distributed about the circumference of the catheter shaft. It was found that when balloon material is arranged in a manner similar to that shown in FIGS. 6A-6C, there was less non-uniformity in the expanded scaffold and less instances of cracks or fractures in scaffold struts caused by over expansion.

Figure 13B:
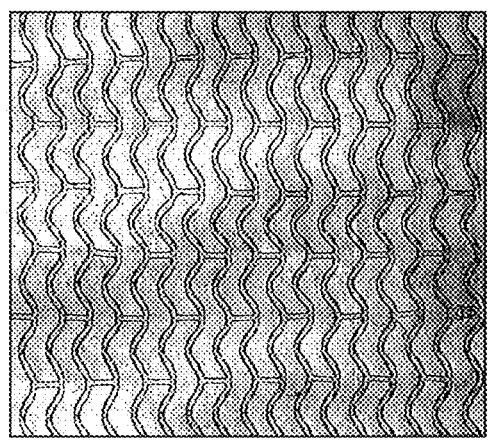
FIG. 13B is a FINESCAN image of a scaffold having a pattern similar to that shown in FIG. 7. The scaffold was crimped using the process of FIGS. 4A-4B. The scaffold was then expanded by inflation of the balloon. As shown in this image, the scaffold exhibits a more uniform expansion than the scaffold in FIG. 13A.

FIG. 13B shows a FINESCAN image of a scaffold expanded after being crimped using the process of FIGS. 4A-4B. FIG. 12 shows a perspective view of scaffold expanded after crimping using this process. As can be appreciated by comparing these photographs to FIGS. 13A and 10, respectively, when crimped using the FIGS. 4A-4B process the scaffold expands more uniformly than when the scaffold is crimped using the process of FIGS. 1A-1B.

EXAMPLE 4

Figure 5A:
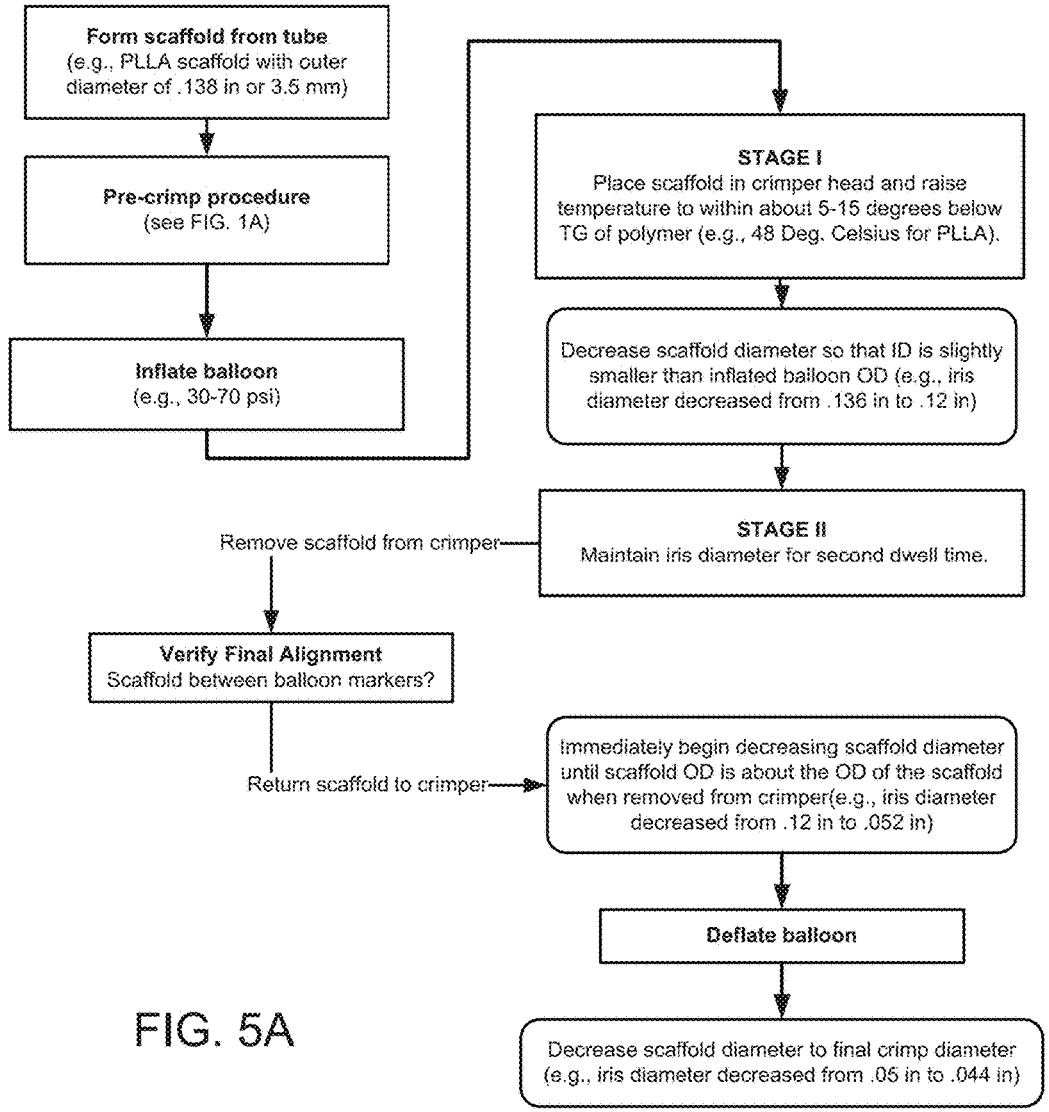
FIG. 5A is another example of a flow process for crimping a polymer scaffold to a balloon.
Figure 5B:
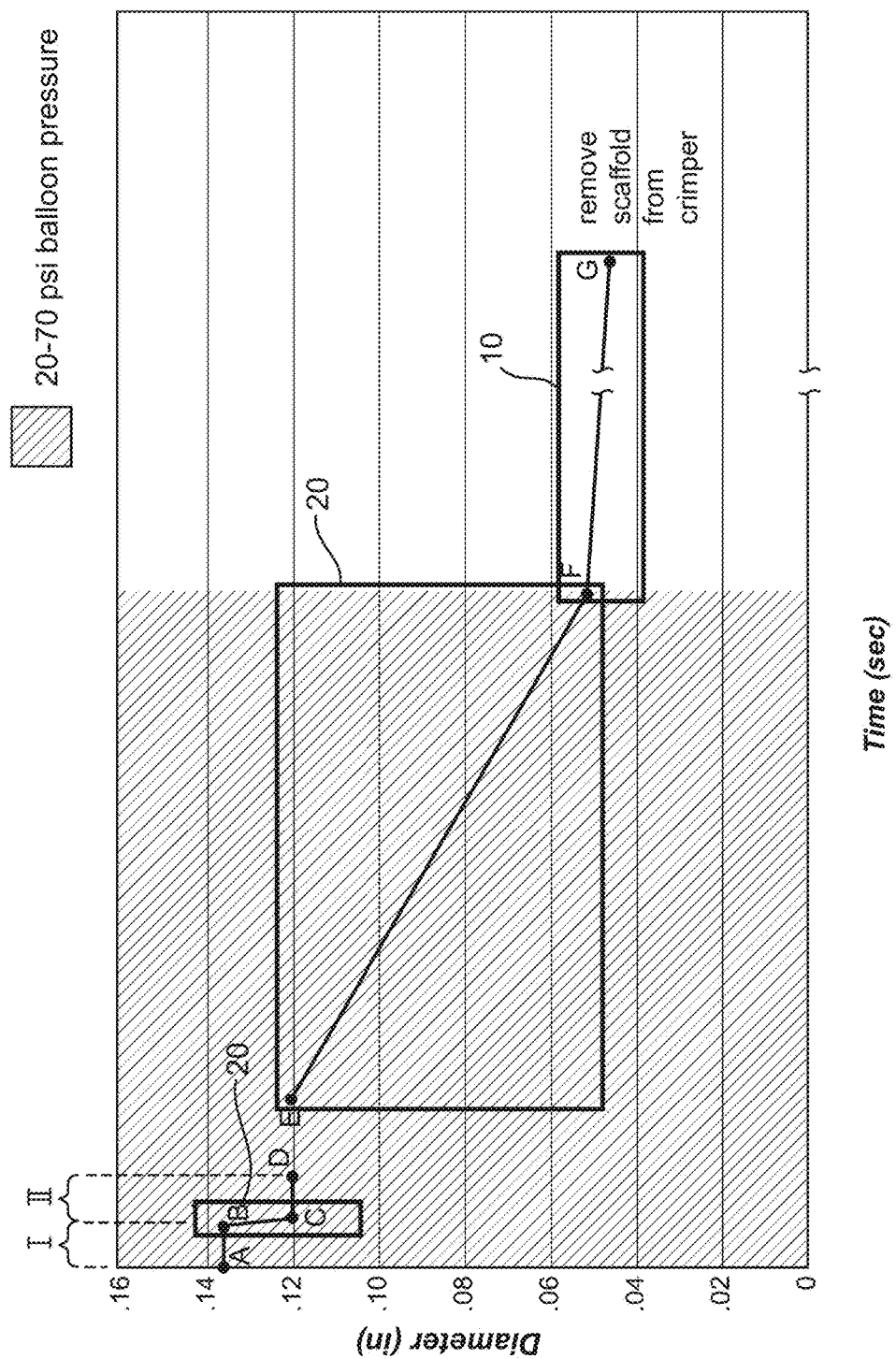
FIG. 5B shows the crimping portion of the FIG. 5A flow process in graphical form, plotting scaffold diameter vs. time and indicating the balloon pressure supplied during steps of the crimping process.

FIGS. 5A-5B illustrate the steps associated with another example of a crimping process according to the preferred embodiments. FIG. 5B illustrates in graphical form the crimping portion of the FIG. 5A flow—a graph of scaffold diameter verses time. As with the previous example, a balloon pressure of between about 20-70 psi is applied throughout substantially all of the crimping process. In this case, balloon pressure is maintained until the scaffold diameter has reached about 35% of its pre-crimp diameter. Additionally, in this example, following the final alignment check the iris diameter is continuously reduced at a slow rate until reaching the final crimping diameter.

Stage I:

The scaffold supported on the inflated balloon of the balloon-catheter is placed within the crimp head. The balloon when inflated and supporting the scaffold in this manner preferably has substantially all folds removed.

After the scaffold reaches the crimping temperature, the iris of the crimper closes to reduce the scaffold inner diameter (ID) is slightly less than the outer diameter (OD) of the pressurized balloon (e.g., from 0.136 in (3.5 mm) to about 0.12 in, or about a 15% diameter reduction).

Stage II:

The crimper jaws are held at the 0.12 in diameter and maintained at this diameter for a second dwell period at the crimping temperature.

Final Alignment Step:

After the second dwell period is complete, the scaffold and balloon are removed from the crimper to check the scaffold alignment on the balloon.

After Stage II, the scaffold's diameter has been reduced to about 80-85% of its starting diameter (as in the prior example).

The scaffold and balloon are returned to the crimper. The jaws are closed to a diameter of about 0.12 in, which may be slightly less than the scaffold OD when it is removed from the crimper (to check alignment) and recoils slightly. The iris diameter is then reduced slowly from 0.12 in to about 0.05 in (e.g., 0.07 in over a period of about 100-120 seconds) to allow the visco-elastic material to deform without cracking. The diameter reduction during this step is about 40%. This diameter reduction following the alignment check may alternatively correspond to about the diameter of the scaffold when the scaffold is removed from the restraining sheath at the point of use.

When the about 0.05 iris diameter is reached, the balloon pressure is relieved while the iris diameter continues to slowly decrease until it reaches a 0.044 in diameter. When reaching the 0.044 diameter the scaffold is removed from the crimper and a retaining sheath is placed over the scaffold to reduce recoil.

In a similar manner to the previous example, by inflating the balloon before any crimping and maintaining balloon pressure until the iris diameter reaches about 0.05 in it is believed that this preferred crimping process will increase scaffold-balloon retention forces and result in more uniform expansion of the scaffold.

Preferred Scaffold Pattern

As noted above, in a preferred embodiment a scaffold has the pattern described in U.S. application Ser. No. 12/447,758 (US 2010/0004735) to Yang & Jow, et al. Other examples of scaffold patterns suitable for PLLA are found in US 2008/0275537. FIG. 7 shows a detailed view of an intermediate portion 216 of a strut pattern 200 depicted in US 2010/0004735. The intermediate portion includes rings 212 with linear ring struts 230 and curved hinge elements 232. The ring struts 230 are connected to each other by hinge elements 232. The hinge elements 232 are adapted to flex, which allows the rings 212 to move from a non-deformed configuration to a deformed configuration. Line B-B lies on a reference plane perpendicular to the central axis 224 depicted in US 2010/0004735. When the rings 212 are in the non-deformed configuration, each ring strut 230 is oriented at a non-zero angle X relative to the reference plane. The non-zero angle X is between 20 degrees and 30 degrees, and more narrowly at or about 25 degrees. Also, the ring struts 230 are oriented at an interior angle Y relative to each other prior to crimping. The interior angle Y is between 120 degrees and 130 degrees, and more narrowly at or about 125 degrees. In combination with other factors such as radial expansion, having the interior angle be at least 120 degrees results in high hoop strength when the scaffold is deployed. Having the interior angle be less than 180 degrees allows the scaffold to be crimped while minimizing damage to the scaffold struts during crimping, and may also allow for expansion of the scaffold to a deployed diameter that is greater than its initial diameter prior to crimping. Link struts 234 connect the rings 212. The link struts 234 are oriented parallel or substantially parallel to a bore axis of the scaffold. The ring struts 230, hinge elements 232, and link struts 234 define a plurality of W-shape closed cells 236. The boundary or perimeter of one W-shape closed cell 236 is darkened in FIG. 2 for clarity. In FIG. 7, the W-shapes appear rotated 90 degrees counterclockwise. Each of the W-shape closed cells 236 is immediately surrounded by six other W-shape closed cells 236, meaning that the perimeter of each W-shape closed cell 236 merges with a portion of the perimeter of six other W-shape closed cells 236. Each W-shape closed cell 236 abuts or touches six other W-shape closed cells 236.

Referring to FIG. 7, the perimeter of each W-shape closed cell 236 includes eight of the ring struts 230, two of the link struts 234, and ten of the hinge elements 232. Four of the eight ring struts form a proximal side of the cell perimeter and the other four ring struts form a distal side of the cell perimeter. The opposing ring struts on the proximal and distal sides are parallel or substantially parallel to each other. Within each of the hinge elements 232 there is an intersection point 238 toward which the ring struts 230 and link struts 234 converge. There is an intersection point 238 adjacent each end of the ring struts 230 and link struts 234. Distances 240 between the intersection points adjacent the ends of rings struts 230 are the same or substantially the same for each ring strut 230 in the intermediate portion 216 of the strut pattern 200. The distances 242 are the same or substantially the same for each link strut 234 in the intermediate portion 216. The ring struts 230 have widths 237 that are uniform in dimension along the individual lengthwise axis 213 of the ring strut. The ring strut widths 234 are between 0.15 mm and 0.18 mm, and more narrowly at or about 0.165 mm. The link struts 234 have widths 239 that are also uniform in dimension along the individual lengthwise axis 213 of the link strut. The link strut widths 239 are between 0.11 mm and 0.14 mm, and more narrowly at or about 0.127 mm. The ring struts 230 and link struts 234 have the same or substantially the same thickness in the radial direction, which is between 0.10 mm and 0.18 mm, and more narrowly at or about 0.152 mm.

As shown in FIG. 7, the interior space of each W-shape closed cell 236 has an axial dimension 244 parallel to line A-A and a circumferential dimension 246 parallel to line B-B. The axial dimension 244 is constant or substantially constant with respect to circumferential position within each W-shape closed cell 236 of the intermediate portion 216. That is, axial dimensions 244A adjacent the top and bottom ends of the cells 236 are the same or substantially the same as axial dimensions 244B further away from the ends. The axial and circumferential dimensions 244, 246 are the same among the W-shape closed cells 236 in the intermediate portion 216.

It will be appreciated from FIG. 7 that the strut pattern for a scaffold that comprises linear ring struts 230 and linear link struts 234 formed from a radially expanded and axially extended polymer tube. The ring struts 230 define a plurality of rings 212 capable of moving from a non-deformed configuration to a deformed configuration. Each ring has a center point, and at least two of the center points define the scaffold central axis. The link struts 234 are oriented parallel or substantially parallel to the scaffold central axis. The link struts 234 connect the rings 212 together. The link struts 232 and the ring struts 230 defining W-shape closed cells 236. Each W-shaped cell 236 abuts other W-shaped cells. The ring struts 230 and hinge elements 232 on each ring 212 define a series of crests and troughs that alternate with each other. Each crest on each ring 212 is connected by one of the link struts 234 to another crest on an immediately adjacent ring, thereby forming an offset "brick" arrangement of the W-shaped cells.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the claims should not be construed to limit the invention to the specific embodiments disclosed in the specification. Rather, the scope of the invention is to be determined entirely by the claims, which are to be construed in accordance with established doctrines of claim interpretation.

What is claimed is:

1. A method, comprising:
   using a scaffold having a diameter and made from a tube comprising a polymer having a glass transition temperature (TG);
   using a balloon having pre-arranged folds; and
   crimping the scaffold to the balloon, including the steps of:
      inflating the balloon, and
      while the balloon is inflated and the scaffold has a crimping temperature of between TG and 15 degrees C. below TG, reducing the diameter from a starting size to a first size;
   wherein the crimping step further includes:
      a first dwell period after the diameter is reduced to the first size, and
      an additional 60%-70% reduction in the diameter, relative to the first size, after the first dwell period.

2. The method of claim 1, wherein there is no dwell period during the additional 60%-70% diameter reduction.

3. The method of claim 1, wherein after the additional 60%-70% diameter reduction none of the pre-arranged folds are present in the balloon.

4. The method of claim 1, wherein the crimping includes only one dwell period.

5. The method of claim 1, wherein the balloon is inflated to about 20-80% of a nominal balloon inflation pressure, or about 10-30% of an over-inflated or maximum inflation pressure for the balloon.

6. The method of claim 1, wherein after the crimping step the scaffold is crimped to the balloon, wherein the crimped scaffold is retained to the balloon by a retention force of about 1.32 lb., about 1.63 lb., about 1.43 lb., about 1.56 lb. or about 1.55 lb.

7. A method, comprising:
   using a scaffold having a diameter and made from a tube comprising a polymer having a glass transition temperature (TG), wherein the scaffold diameter has a starting size;
   using a balloon having a nominal inflation diameter that is less than the starting size; and
   crimping the scaffold to the balloon, including the steps of:
      heating the scaffold to an elevated temperature that is below TG,
      inflating the balloon to a crimping pressure that is 20% to 80% of a nominal inflation pressure for the balloon, and
      while the balloon has the crimping pressure, reducing the scaffold diameter from the starting size to a first size less than the nominal inflation diameter.

8. A method, comprising:
   using a scaffold having a diameter and made from a tube comprising a polymer having a glass transition temperature (TG), the scaffold diameter having a starting size;
   using a balloon having a nominal inflation diameter that is less than the starting size; and
   crimping the scaffold to the balloon while the scaffold has a crimping temperature of between TG and 15 degrees C. below TG, including the steps of:
      (a) inflating the balloon,
      (b) reducing the scaffold diameter from the starting size to a first size that is less than the nominal inflation diameter, and
      (c) after step (b) reducing the scaffold diameter by an additional 60%-70% relative to the first size, and there is no dwell period when the scaffold diameter is being reduced by the additional 60%-70%.

9. The method of claim 8, wherein there is only one dwell period during the crimping.

10. The method of claim 8, wherein the balloon has pre-arranged folds prior to inflation, and when the balloon is inflated substantially all folds are removed from the balloon.

11. The method of claim 8, further including using a crimper device to reduce the scaffold diameter from the starting size to the first size, wherein the scaffold is removed from the crimper device after the scaffold diameter is reduced to the first size, followed by returning the scaffold to the crimping device, whereupon the scaffold diameter is reduced by the additional 60%-70% relative to the first size.

12. The method of claim 8, further including placing the scaffold within a sheath, wherein the scaffold diameter size is 35%-40% of the starting size when inside the sheath.

13. The method of claim 8, wherein the polymer comprises Poly (L-lactide) or Poly(lactide-co-glycolide).

14. The method of claim 8, wherein the polymer comprises Poly(lactide-co-glycolide) (PLGA), the crimping temperature is about 43 to 54 degrees C. and the glycolide content of PLGA is between about 15% to 0%.

15. The method of claim 7, wherein after the crimping step the scaffold is crimped to the balloon, wherein the crimped scaffold is retained to the balloon by a retention force of about 1.32 lb., about 1.63 lb., about 1.43 lb., about 1.56 lb. or about 1.55 lb.

16. The method of claim 15, wherein the scaffold is heated to a temperature of between TG and 15 Deg C. below TG.

17. The method of claim 15, wherein the scaffold diameter is reduced from the starting size to the first size using a crimping device, further including the steps of:
   removing the scaffold from the crimping device after the scaffold diameter is reduced to the first size, then returning the scaffold to the crimping device, and
   after the returning the scaffold to the crimping device, reducing the scaffold diameter to a second size, less than the first size, using the crimping device.

18. The method of claim 17, wherein the second size is between 30% and 40% of the first size.

19. The method of claim 15, further including reducing the scaffold diameter to a second size less than the first size.

20. The method of claim 15, wherein the balloon has pre-arranged folds prior to inflation, and when the balloon is inflated substantially all folds are removed from the balloon.

21. The method of claim 15, further including using a crimper device to reduce the scaffold diameter from the starting size to the first size, followed by reducing the scaffold diameter to a second size, less than the first size, removing the scaffold from the crimping device after the scaffold diameter is reduced to the second size, and placing the scaffold in a sheath,
   wherein the scaffold diameter has a third size that is 35-40% of the starting size when the scaffold is inside the sheath.

22. The method of claim 15, wherein the polymer comprises Poly (L-lactide) or Poly(lactide-co-glycolide).

23. The method of claim 8, wherein after the crimping step the scaffold is crimped to the balloon, wherein the crimped scaffold is retained to the balloon by a retention force of about 1.32 lb., about 1.63 lb., about 1.43 lb., about 1.56 lb. or about 1.55 lb.

\* \* \* \* \*